US011518408B2

(12) United States Patent
Arechiga-Gonzalez et al.

(10) Patent No.: US 11,518,408 B2
(45) Date of Patent: Dec. 6, 2022

(54) PREDICTIVE IMPAIRMENT MONITOR SYSTEM AND METHOD

(71) Applicant: TOYOTA RESEARCH INSTITUTE, INC., Los Altos, CA (US)

(72) Inventors: Nikos Arechiga-Gonzalez, San Mateo, CA (US); Soonho Kong, Arlington, MA (US); Jonathan Decastro, Arlington, MA (US); Frank Permenter, Cambridge, MA (US); Dennis Park, Fremont, CA (US)

(73) Assignee: TOYOTA RESEARCH INSTITUTE, INC., Los Altos, CA (US)

( * ) Notice: Subject to any disclaimer, the term of this patent is extended or adjusted under 35 U.S.C. 154(b) by 209 days.

(21) Appl. No.: 17/097,580

(22) Filed: Nov. 13, 2020

(65) Prior Publication Data

US 2022/0153302 A1   May 19, 2022

(51) Int. Cl.
*B60Q 1/00* (2006.01)
*B60W 60/00* (2020.01)
(Continued)

(52) U.S. Cl.
CPC ....... *B60W 60/0015* (2020.02); *A61B 5/0077* (2013.01); *A61B 5/18* (2013.01); *A61B 5/4848* (2013.01); *A61B 5/7264* (2013.01); *B60W 30/181* (2013.01); *B60W 40/09* (2013.01); *B60W 50/14* (2013.01); *G06K 9/6256* (2013.01); *G06V 20/597* (2022.01); *G06V 40/171* (2022.01); *G06V 40/176* (2022.01); *B60W 2040/0845* (2013.01);
(Continued)

(58) Field of Classification Search
CPC .......... B60W 60/0015; B60W 30/181; B60W 40/09; B60W 50/14; B60W 2540/043; B60W 2540/225; B60W 2540/221; B60W 2040/0845; B60W 2050/146; B60W 2420/42; B60W 2540/24; G06V 40/171; G06V 20/597; G06V 40/176; A61B 5/0077; A61B 5/18; A61B 5/4848; A61B 5/7264; G06K 9/6256
USPC .......................................... 701/27; 340/439
See application file for complete search history.

(56) References Cited

U.S. PATENT DOCUMENTS 9,302,584 B2   4/2016   Walsh et al.
10,065,658 B2   9/2018   Deligianni et al.
(Continued)

*Primary Examiner* — Naomi J Small
(74) *Attorney, Agent, or Firm* — Oblon, McClelland, Maier & Neustadt, L.L.P.

(57) ABSTRACT

A driver monitor system and method for predicting impairment of a user of a vehicle. The system includes video cameras, an input device for inputting a list of medications being taken by the driver. Processing circuitry predicts side effects of the medications based on the half-life of the medication, detecting eye gaze movement, eye lid position, and facial expression of the user using images from the video camera, predicting whether the user is transitioning into an impaired physical state that is a side effect of the medications, verifying the side effect of the medications, determining whether the user is fit to drive using the verified side effects of the medications, and outputting to the vehicle an instruction to operate the vehicle in a level of automation that makes up for the at least one side effect or to perform a safe pull over operation of the vehicle.

20 Claims, 21 Drawing Sheets

(51) Int. Cl.
*G06K 9/62* (2022.01)
*B60W 40/09* (2012.01)
*B60W 50/14* (2020.01)
*B60W 30/18* (2012.01)
*A61B 5/18* (2006.01)
*A61B 5/00* (2006.01)
*G06V 20/59* (2022.01)
*G06V 40/16* (2022.01)
*B60W 40/08* (2012.01)

(52) U.S. Cl.
CPC ... *B60W 2050/146* (2013.01); *B60W 2420/42* (2013.01); *B60W 2540/043* (2020.02); *B60W 2540/221* (2020.02); *B60W 2540/225* (2020.02); *B60W 2540/24* (2013.01)

(56) References Cited

U.S. PATENT DOCUMENTS

| | | |
|---|---|---|
| 10,272,921 B2 | 4/2019 | Edgington et al. |
| 2016/0103338 A1* | 4/2016 | Hart ..................... A61B 3/112 351/206 |
| 2017/0355377 A1* | 12/2017 | Vijaya Kumar .. B60W 50/0098 |
| 2018/0079278 A1* | 3/2018 | Kirpichnikov ..... B60H 1/00742 |
| 2019/0202464 A1 | 7/2019 | McGill |

* cited by examiner

PREDICTIVE IMPAIRMENT MONITOR SYSTEM AND METHOD

BACKGROUND

Technical Field

The present disclosure is directed to a software application and vehicle system that utilizes information of medications being taken by the driver in order to predict whether or not the driver can operate the vehicle, and can monitor conditions of the driver to determine whether the conditions may be side effects of a medication. The vehicle system may take corrective action when the conditions of the driver are side effects of a medication.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Driving under the influence of prescription drugs, some over-the-counter (OTC) drugs, and some herbal products, may potentially be unsafe due to side effects such as drowsiness, slowed reaction times, and coordination difficulties. For certain types of prescription drugs, over-the-counter drugs, and even certain herbel products. driving may be just as dangerous as driving under the influence of alcohol. Similar to alcohol, certain types of drugs and herbel products can directly affect a driver's ability to drive safely.

Drivers may be unaware of the side effects of medications they are taking and typically believe that side effects will only occur when they are taken in excess. Drivers may be unable to accurately self-assess their impairment when taking medication.

Many prescription medications that are used to control the symptoms of anxiety and depression (Antidepressants and Antianxiety Agents), such as selective serotonin reuptake inhibitors (SSRI), affect the brain and/or judgment. Prescription medications such as Valium and Xanax may have a tranquilizing effect that can impair judgment and reaction times. For example, taking 10 mg of diazepam (Valium) can cause impairment similar to having a blood alcohol content of 0.10%, which is above the legal limit for driving. Antihistamines have a potential driving impairment due to a threat of anticholinergic cognitive issues. Although OTC medications like Claritin, Allegra, and Zyrtec are now manufactured as non-drowsy, not all antihistamine medications are non-drowsy. Patients may not be aware of the effects of the particular antihistamine they are taking and may just assume that most antihistamines are non-drowsy. Also, antihistamines can cause blurred vision because they dry up the tear ducts. Antihypertensives (Blood pressure medications) may have side effects such as lightheadedness, dizziness, and fatigue that can hinder driving performance. Also, beta-blockers and sympatholytic drugs like clonidine, guanfacine, and methyldopa may cause sedation, confusion, or insomnia. Most antipsychotic agents may impair driving performance through various central nervous system (CNS) effects. In particular, antipsychotics generally have 3 side effects including sedation, anticholinergic effects, and extrapyramidal effects that can directly affect a patient's ability to drive. Benzodiazepines (anti-anxiety drugs) can lead to driving impairments in vision, attention, and motor coordination. Long-acting benzodiazepines can impair psychomotor function the following day.

It is a common misconception that stimulants such as caffeine pills and high caffeine energy drinks such as Red Bull would be good to take before driving. In reality, such stimulants makes a person more impetuous and less likely to pay attention to fine details (i.e., lower ability to concentrate). Also, stimulants combined with alcohol can give a person the worst of both. Despite not feeling as drunk, the alcohol is still impairing a person's ability to drive.

Also, nearly 20 percent of seniors commonly take medications that can impair driving. Medications that are often taken by seniors include benzodiazepines, narcotic pain medications, hypnotics (anti-depressants), and sleep medications. In addition, seniors may unintentionally take multiple medications that have the same effect, amplifying the results to unsafe levels. Some seniors may see a number of physicians and specialists, so they may not be aware of the potentially unsafe dosage levels of multiple medications.

Driver fatigue or drowsiness is a state of a driver characterized by lowering of the eyelids (typically measured by percent of eye closure—PERCLOS), possibly in combination with other signs such as lower heart rate, yawning, and head dropping. Sometimes a driver suffering from driver fatigue or drowsiness may shake his/her head in an effort to fight off fatigue. In some cases, when the vehicle is stopped, such as at a stop light, the driver may close his/hers eyes for a short period in an effort to rest their eyes.

Development is underway in more advanced vehicle safety features with an end goal of achieving autonomous vehicles, or self-driving cars. A range of lowest to highest levels of automation have been defined. The levels of autonomous vehicles may use various external vehicle sensors (e.g., cameras, LiDAR, radar, ultrasonic, GPS, etc.) to scan the external environment. FIG. 1 is a diagram of the range of levels of automated driving. A lowest level of automation (Level 1) relates to features of automatic cruise control 111, advanced emergency braking 113, lane assist 115, and cross traffic alert 117. This level makes use of cameras for surround view object detection 119 to assist in parking a vehicle. A next level (Level 2) includes a greater degree of shared control between automation and the driver of the vehicle, such as where the driver controls steering, but the vehicle has control over engine power and braking to maintain and vary speed. This next level includes a function of traffic jam assist 121 and automatic parking 123. At this next level, automatic parking may include automatic parallel parking, automatic back in parking, or front end parking in a parking spot. Another level of automation (Level 3) includes a condition where the vehicle is under full control but the driver monitors the driving and can intervene at any time, also referred to as conditional automation. This level includes advanced emergency braking in combination with steering 125, highway autopilot 131, and remote parking 133. A higher level of automation (Level 4) may include a city driving autopilot function 141 and a valet parking function 143. At this higher level of automation the driver may turn their attention to other tasks while the vehicle is performing driving control. A highest level of automation (Level 5), via a fully autonomous vehicle, is contemplated in which no human intervention is required to drive the vehicle. The vehicle operates in auto pilot 151 in which it is expected to work on all roads in all weather conditions. Vehicle control systems have been developed that can switch from low levels to greater levels of autonomous driving based on the state of the driver.

U.S. Pat. No. 10,065,658 relates to bias of physical controllers in a system. The system determines the state of a user from user input that includes a calendar of the user, a profile of the user, and/or analysis of audible input from the user. The profile of the user can include a list of medications taken. A controlled action, such as engaging autopilot, may be taken when a threshold condition on the state of the user has been met. In one case, a user may tell a device that he or she has taken, e.g., an antihistamine, and thus a physical controller may vibrate with greater intensity to suggest a possible deviation from expected behavior based on this information. A physical controller may change its sensitivity to resist motions that are closer to a danger zone of use.

U.S. Patent Application Publication 2019/0202464 relates to vehicle systems and methods for detecting and mitigating an incapacitated driver. The disclosed vehicle system determines a specific cause of a driver's incapacitation and operates a vehicle in an at least partially autonomous driving mode based on the specific cause of incapacity. The system determines the cause of the driver's incapacitation based on the driver's behavior as opposed to specific data entries made by the driver.

Methods have been proposed for detecting driver fatigue and applying stimulus to mitigate the fatigued state. U.S. Pat. No. 9,302,584 relates to drowsy driver prevention systems and methods. The disclosed system determines a level of driver drowsiness by monitoring driver behavior, for example, by angle of orientation of the driver's head. Driver profiles may be created that contain a list of medications and such factors may be used to establish thresholds for indicating levels of confidence of driver drowsiness.

Although driver fatigue or drowsiness is a condition which may render a driver not fully fit for driving, medications may have other side effects that may also impair a driver's behavior. As mentioned above, some medications may have an effect in which vision becomes blurry. Other side effects may include dizziness, confusion, reduced attention, and reduced motor skills.

Thus, there is a need for a system and method of predicting driver behavior based on medication that the driver has taken and the half-life of that medication.

An aspect is an apparatus including an input device by which a driver of a vehicle inputs medication being taken by the driver, and a processor that predicts ability of the driver to safely operate the vehicle based on the half-life of the medication and prevents the driver from operating the vehicle based on results of the prediction. An autonomous vehicle or a vehicle having advanced driver-assist features may increase the level of automation or fully take over operation of the vehicle depending on side effects of medications and remaining half-life of the medications.

SUMMARY

An aspect is a driver monitor system for predicting impairment of a user of a vehicle, the system including at least one video camera; an input output device for inputting a list of at least one medication being taken by the user of the vehicle; and processing circuitry configured to: predict at least one side effect of the at least one medication based on the half-life of the at least one medication, detect eye gaze movement, eye lid position, and facial expression of the user using images from the at least one video camera, use the eye gaze movement, eye lid position, and facial expression to predict whether the user is transitioning into an impaired physical state that is a side effect of the at least one medication, verify the at least one side effect of the at least one medication, determine whether the user is fit to drive using the verified at least one side effect of the at least one medication, and output to the vehicle an instruction to operate the vehicle in a level of automation that makes up for the at least one side effect or to perform a safe pull over operation of the vehicle.

An aspect is a method of predicting impairment of a driver of a vehicle by a driver monitor system including at least one video camera, an input output device for inputting a list of at least one medication being taken by the driver of the vehicle, and processing circuitry. The method including predicting at least one side effect of the at least one medication based on the half-life of the at least one medication, detecting, by the processing circuitry, eye gaze movement, eye lid position, and facial expression using images from the at least one video camera; using the eye gaze movement, eye lid position, and facial expression to predict, by the processing circuitry, whether the user is transitioning into an impaired physical state; verifying the at least one side effect of the at least one medication; determining whether the user is fit to drive using the verified at least one side effect of the at least one medication; and outputting to the vehicle an instruction to operate the vehicle in a level of automation that makes up for the at least one side effect or to perform a safe pull over operation of the vehicle.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
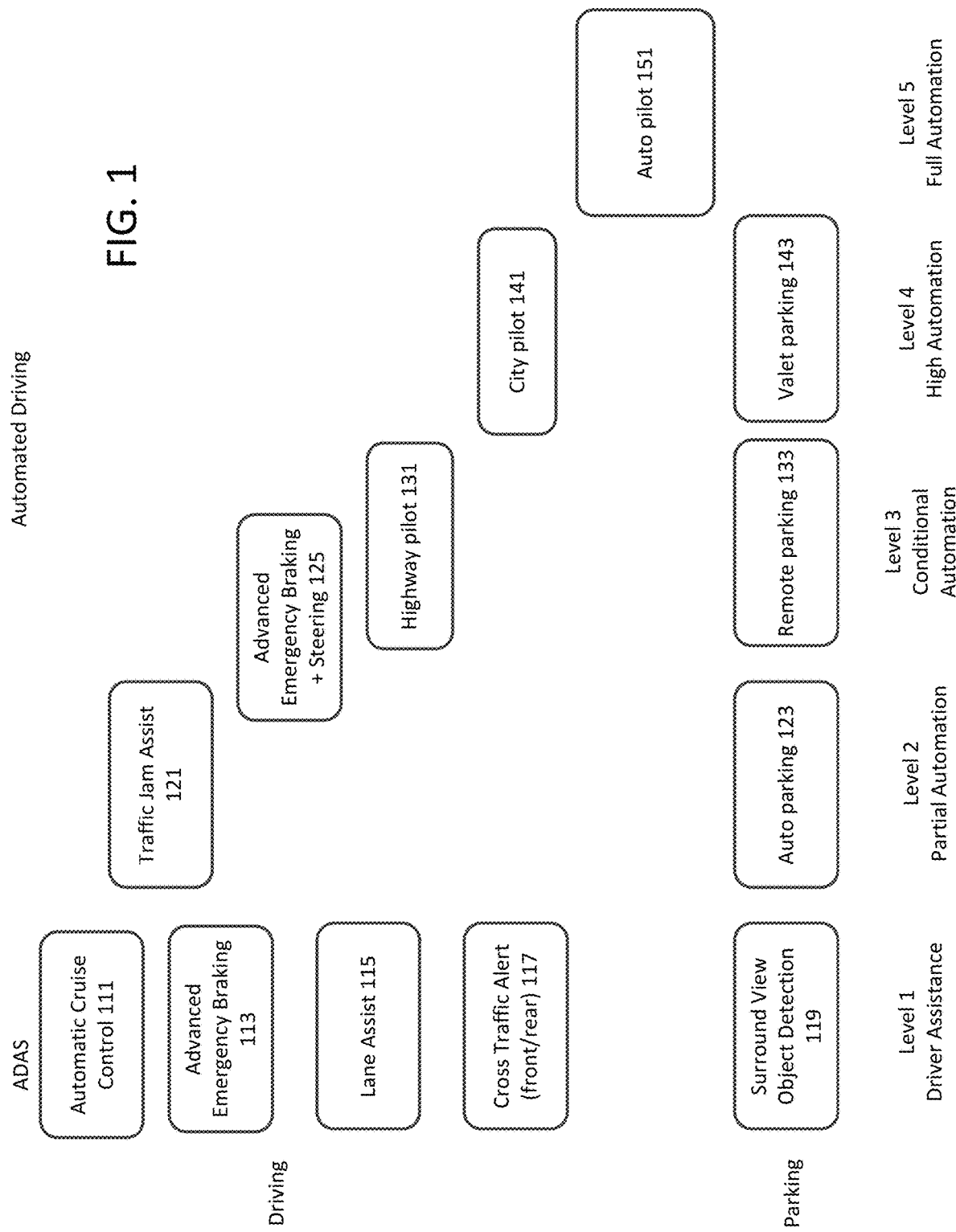
FIG. 1 is a diagram of levels of automated driving.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to a technique that evaluates various medications, predicts side effects, and applies the most appropriate response to the predicted side effect. The system utilizes vehicle sensors (e.g., cameras, blood pressure, heart rate, body temperature, etc.) and machine learning to predict side effects of taken medications based on half-lives.

Figure 2:
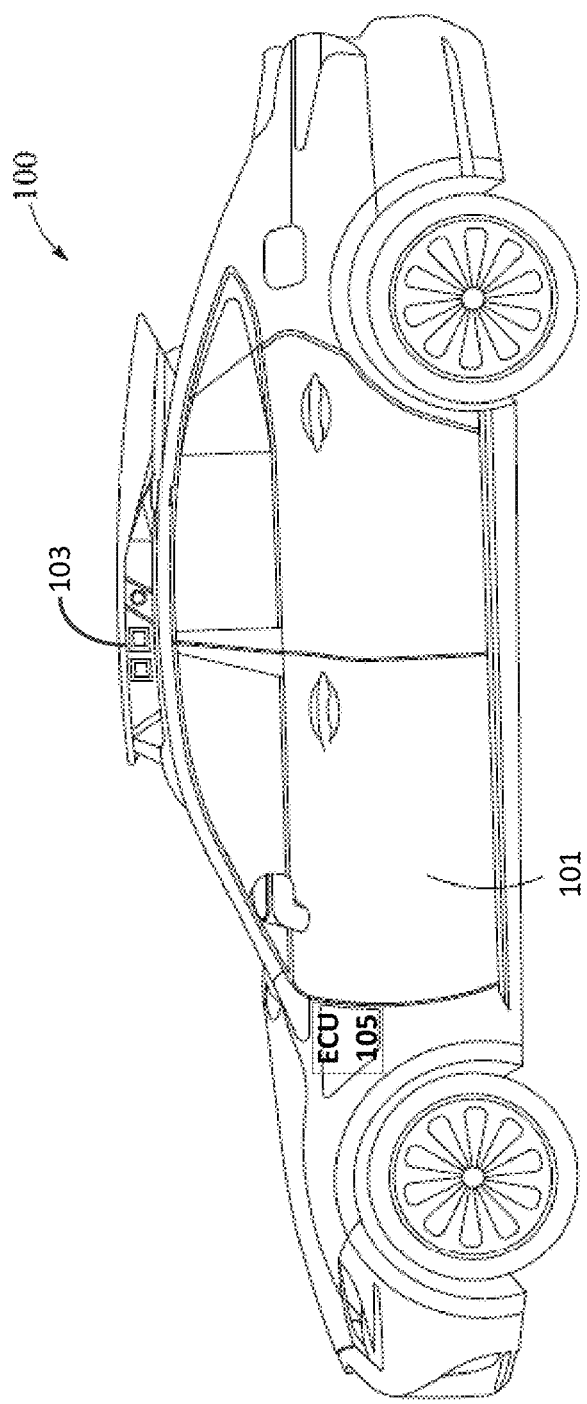
FIG. 2 illustrates a vehicle having an array of exterior sensors.

FIG. 2 illustrates a passenger vehicle having an array of exterior sensors, such as those that may be found in passenger vehicles ranging from those equipped with advanced driver-assist features to those equipped as a fully autonomous vehicle, or self-driving vehicle.

Referring to FIG. 2, a vehicle 100 includes an array of sensors 103 and a controller, ECU 105. Sensors may be mounted on a roof of a vehicle, mounted on the vehicle body 101, and may be included within the body of a passenger vehicle, or a combination thereof. The types of sensors that may be mounted on an exterior of a vehicle may include radar, LiDAR, video cameras, and sonar antennas. Video cameras, radar antennas, and sonar antennas may be located around a periphery of the vehicle. In particular, the passenger vehicle may be fitted with forward-looking cameras to detect traffic signals, as well as front-mounted sensors to detect other vehicles, pedestrians, and obstacles, or to determine traffic conditions, such as intersections and merging traffic lanes, in the vehicle's vicinity. The combination of sensors may be used to assist drivers in choosing the safest routes possible, or may provide information needed for operation of an autonomous vehicle. In particular, a passenger vehicle 100 may include other sensors for advanced control and navigation, including GPS, odometry and internal measurement units.

A passenger vehicle 100 may further include sensors such one or more thermometers for monitoring the cabin environmental conditions at different portions of the interior. The cabin of a vehicle may also include video cameras and infrared thermometer sensors for monitoring persons and other objects within the vehicle cabin. A passenger vehicle may include internal sensors for monitoring various conditions of the vehicle, such as steering angle and vehicle speed. Also, the vehicle engine may include various sensors for pressure, temperature, air flow and engine speed. Tires may include pressure sensors for measuring the tire pressure. Provided readings from some of the sensors, other parameters may be estimated or measured, which are referred to as estimators. For example, fuel usage rate may be estimated based on miles driven and change in fuel level reading. Also, temperature in the cabin may be measured as a heat map that is determined by several infrared thermometers positioned throughout the cabin.

Figure 3:
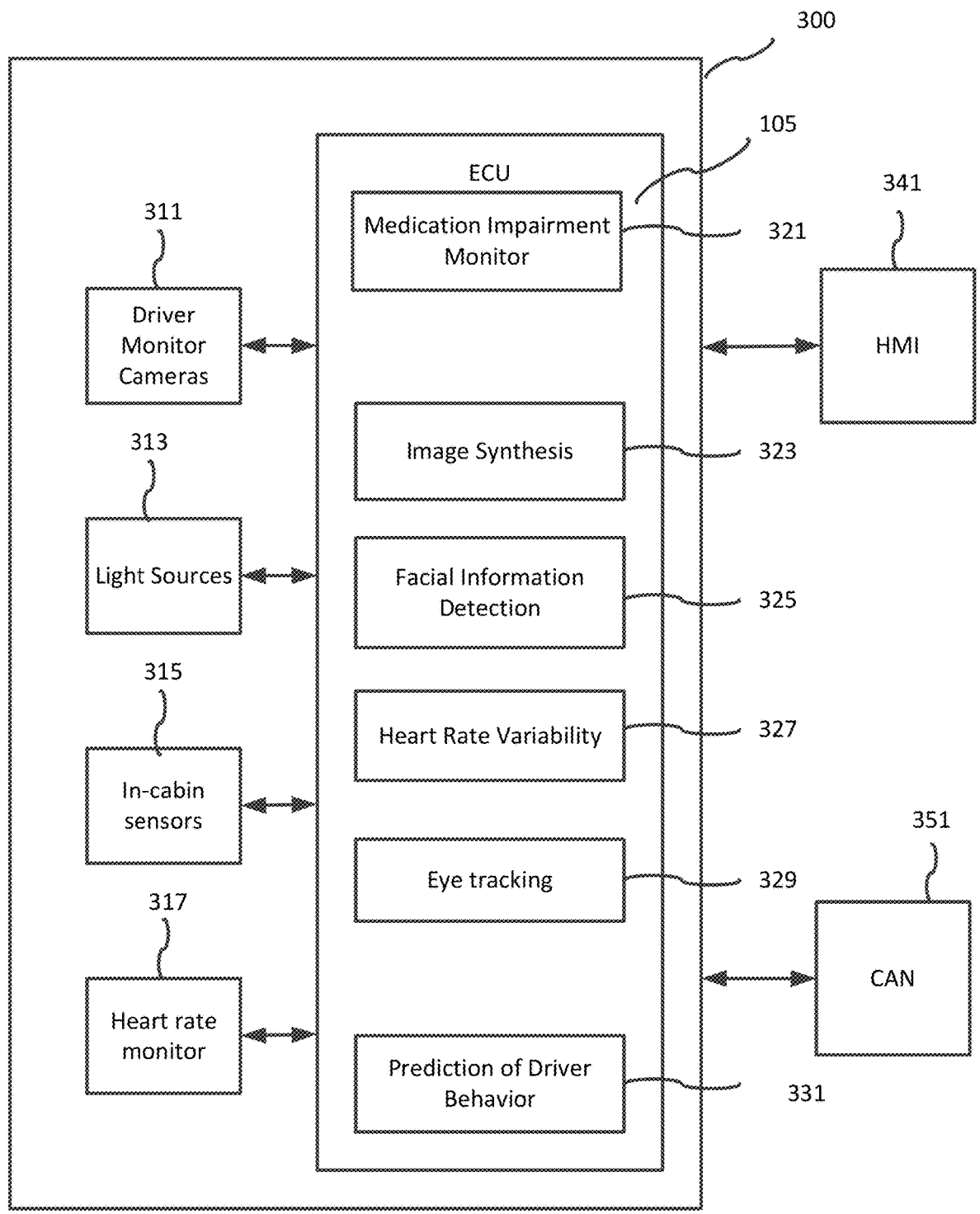
FIG. 3 is a block diagram of driver monitor system in accordance with an exemplary aspect of the disclosure.

FIG. 3 is a block diagram of driver monitor system in accordance with an exemplary aspect of the disclosure. Driver monitor systems may be included in various types of vehicles to enhance driving safety. Passenger vehicles may be driven by drivers that may not have had sufficient sleep or are driving for long periods of time. In a similar manner, trucks may be driven by truck drivers for extended periods of time. Truck driver safety is a concern when the truck driver does not get sufficient rest. Delivery trucks may be faced with driving in heavy traffic conditions and into neighborhoods or congested areas requiring utmost alertness. Thus, driver monitor systems include sensors, such as in-vehicle cameras, to monitor a driver's face, a driver's head position, track the driver's eye movement, the driver's posture in a seat, even other physical state conditions such as heart rate and facial blood flow. The driver monitor systems may include sensors to monitor the vehicle state, such as motion of the steering wheel and position of the vehicle relative to the road. To avoid driver distraction, the lighting for in-vehicle cameras may be infrared lighting.

Although a driver monitor system may be considered most beneficial for low levels of automated driving where the driver is required to control most driving functions, higher levels of automated driving also require alertness of the driver particularly in situations where the driver must take over a driving control function possibly due to an emergency situation. For example, a Level 3 vehicle may encounter emergency situations on a highway that are beyond the capabilities of the automated driving.

Regarding FIG. 3, the driver monitor system 300 may include one or more in-cabin cameras 311 and associated light sources 313. The driver monitor cameras 311 and light sources 313 may be located at various positions in the cabin interior. The driver monitor cameras 311 may capture video images for different functions. At least two driver monitor cameras 311 may capture images of the driver's face and/or head. At least one driver monitor camera 311 may capture images of the driver's body posture while seated. At least one driver monitor camera 311 may be part of an eye tracking system.

The driver monitor system 300 may include other in-cabin sensors 315 for detecting the state of the driver or condition of the cabin environment, such as one or more touch free thermometers. The driver monitor system 300 may include a heart rate monitor 317. The heart rate monitor 317 may be a device worn by a driver, such as a smart watch that includes a heart rate monitoring function. The heart rate monitor 317 may include sensors built into the vehicle, such as heart rate sensors positioned around the perimeter of a steering wheel. The heart rate monitor 317 may be a camera that monitors blood flow to the face. The heart rate monitor 317 may include an operation to store a heart rate profile in a memory in order to perform further analysis of the heart rate such as heart rate variability analysis.

The driver monitor system 300 may include at least one electronic control unit (ECU) 105. The electronic control unit 105 may perform various functions using data received from the sensors 311, 315, 317. An image synthesis function 323 may combine images received from one or more driver monitor cameras 311. The image synthesis function 323 may combine images to form a single synthesized image without overlap. Alternatively, the image synthesis function 323 may combine two or more images to form a three dimensional image. The three dimensional image may be of a driver's face, or of a driver's head.

A facial information detection function 325 may use one or more images received from driver monitor cameras 311 and detect features of the driver's face including eyes, nose, mouth, and possibly ears. Detected facial features may include the position of the eyes, nose and mouth, and whether both ears are visible. Detected features may include whether the driver's mouth is open, or that the driver is yawning. The facial information detection function 325 may determine the position and/or movement of the driver's head.

The heartrate monitor 317 is a sensor that provides a signal that represents a driver's heart rate. A heart rate monitor may use optical technology, which sends light into the person's skin and reads the light coming back in to track pulse. A pulse oximeter detects pulse by illuminating the skin with light from a light-emitting diode and then measuring the amount of light reflected to a photodiode as a photoplethysmographic (PPG) signal. Other heart rate monitors measure heart rate with a transmitter that detects electrical activity.

A heart rate variability function 327 may receive the heart rate signal and perform an analysis to determine variability of the heart rate signal. Hear rate variability (HRV) is the physiological phenomenon of variation in the time interval between heartbeats. It is measured by the variation in the beat-to-beat interval. HRV may be measured by obtaining a continuous heart rate signal, or by acquiring the PPG signal. Among methods of analyzing heart rate variability are time domain methods or frequency-domain methods. Frequency domain methods assign bands of frequency and then count the number of intervals between normal beats (NN) that match each band. The bands are typically high frequency (HF) from 0.15 to 0.4 Hz, low frequency (LF) from 0.04 to 0.15 Hz, and the very low frequency (VLF) from 0.0033 to 0.04 Hz.

An eye tracking function 329 measures either the point of gaze (where one is looking) or the motion of an eye relative to the head. An eye tracker is a device for measuring eye positions and eye movement. Video-based eye trackers typically use the corneal reflection (the first Purkinje image) and the center of the pupil as features to track over time.

Provided medication information, including medication half-life, facial information from the facial information detection function 325, heart rate variability, gaze and eye movement, state of the eye lid, a driver behavior prediction function 331 may be used to predict whether a driver is getting tired, may suffer from dizziness or fainting, may be unable to concentrate, or may be transitioning to any other reduced cognitive state that may be a result of side effects from medications being taken. As will be discussed further below, driver behavior prediction may be implemented using a machine learning technique.

It has been determined that heart rate variability (HRV) is lower than a resting state when a person is in a decreased cognitive state. A fatigued state will likely have a slower heartbeat compared to baseline/norm. Another cognitive state may be characterized by a low HRV.

The eye tracking function 329 may be configured to measure PERCLOS, which is a measure of the percent of eyelid closure. A PERCLOSE measurement may also be used to detect a fatigue state or another cognitive state. Some cognitive states may have a low PERCLOS, while a fatigued state will generally have a higher PERCLOS (drooping eyelids). The eye tracking function 329 may be implemented with a high definition video camera 311.

The eye tracking function 329 may also be configured to perform various other measurements including pupil dilation, saccade, and gaze eccentricity. Saccades serve as a mechanism for fixation, rapid eye movement. When scanning immediate surroundings or reading, human eyes make saccadic movements and stop several times, moving very quickly between each stop. Human eyes move around, locating interesting parts of a scene and building up a mental, three-dimensional map corresponding to the scene. Measurements of saccade may include saccade velocity, acceleration, and frequency.

The eye tracking function 329 may be configured to perform measurements of eye gaze eccentricity, which is a deviation in the driver's gaze. Measurements may also include duration of eye gaze.

A driver monitor camera may also be configured to differentiate a cognitive tunneling state from a fatigued state by its ability to recognize yawning and other facial traits associated with sleepiness, such as eyebrow furrowing.

Lateral movement of a steering wheel may also be used to detect driver fatigue state and other reduced cognitive states. Measurements of steering wheel movement may include steering entropy; steering wheel velocity and acceleration, and steering wheel reversal frequency. When a driver is in a tunneling state, the steering wheel may be unusually fixated. When a driver is in a fatigue state, movements of the steering wheel may be unusually larger than normal.

A human machine interface (HMI) 341 may include devices for visual and audio outputs as well as computer processing circuitry for navigation and infotainment.

A controller area network (CAN) 351 is a network that allows controllers and devices in a vehicle to communicate with each other without a host computer. Among other things, a CAN 351 may provide information about the performance of a vehicle, such as the wheel angle, vehicle speed and acceleration.

Figure 4:
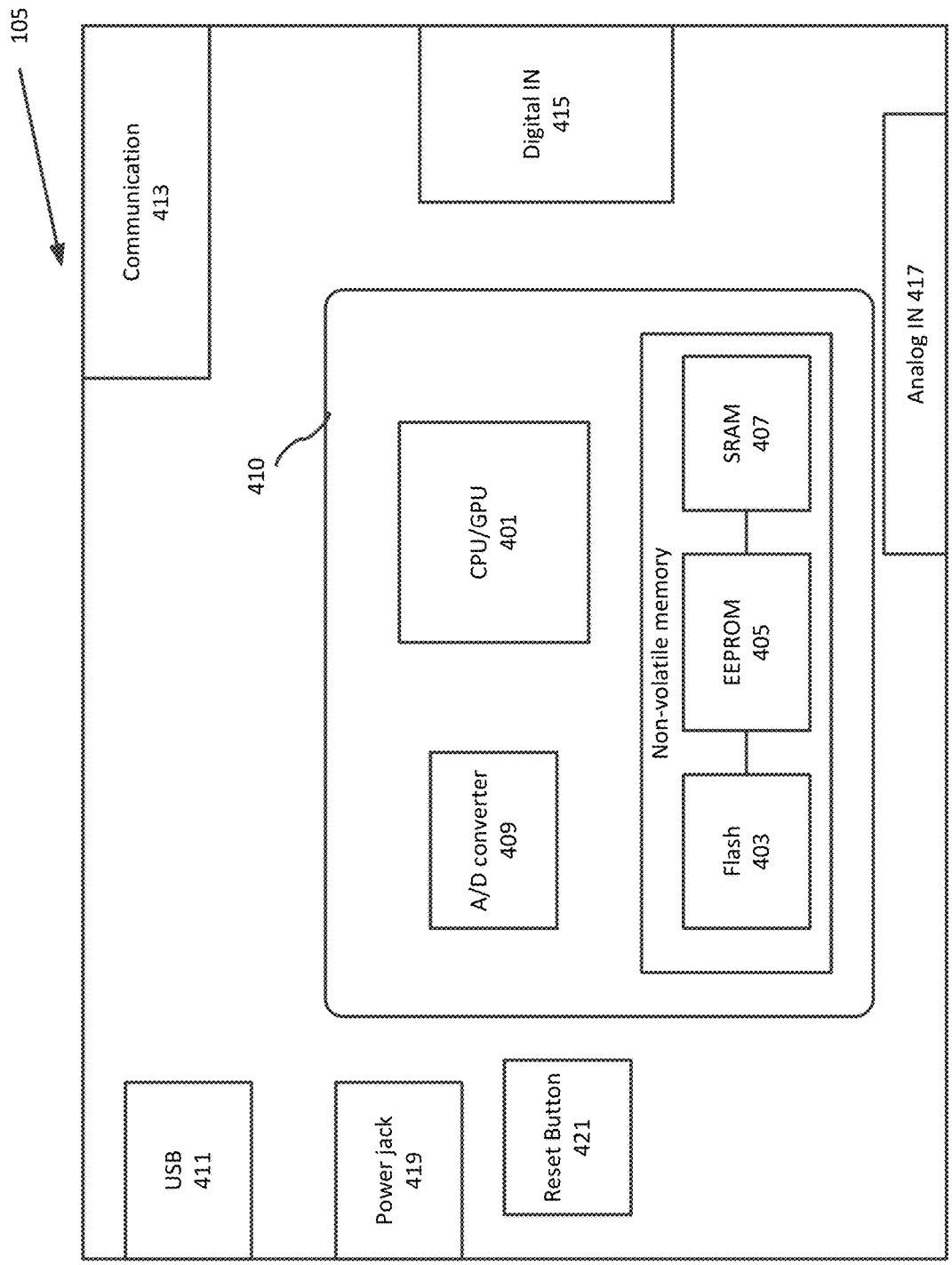
FIG. 4 is a block diagram of an electronic control unit in accordance with an exemplary aspect of the disclosure.

FIG. 4 is a block diagram of an electronic control unit in accordance with an exemplary aspect of the disclosure. The electronic control unit 105 may be based on a microcontroller. A microcontroller includes processing circuitry that may contain one or more processor cores (CPUs) along with memory (volatile and non-volatile) and programmable input/output peripherals. Program memory in the form of flash, ROM, EPROM, or EEPROM is typically included on chip, as well as a secondary RAM for data storage. In one embodiment, the electronic control unit 105 is an integrated circuit board with a microcontroller 410. The board includes digital I/O pins 315, analog inputs 417, hardware serial ports 413, a USB connection 411, a power jack 419, and a reset button 421. Other microcontroller configurations are possible. Variations can include the number of pins, whether or not the board includes communication ports or a reset button.

In an exemplary embodiment, the microcontroller may be a RISC-based microcontroller having flash memory 403, SRAM 407, EEPROM 405, general purpose I/O lines, general purpose registers, a real time counter, six flexible timer/counters, an A/D converter 409, and a JTAG interface for on-chip debugging. It should be understood that other microcontrollers may be used. Microcontrollers vary based on the number of processing cores, size of non-volatile memory, the size of data memory, as well as whether or not it includes an A/D converter or D/A converter.

Figure 5:
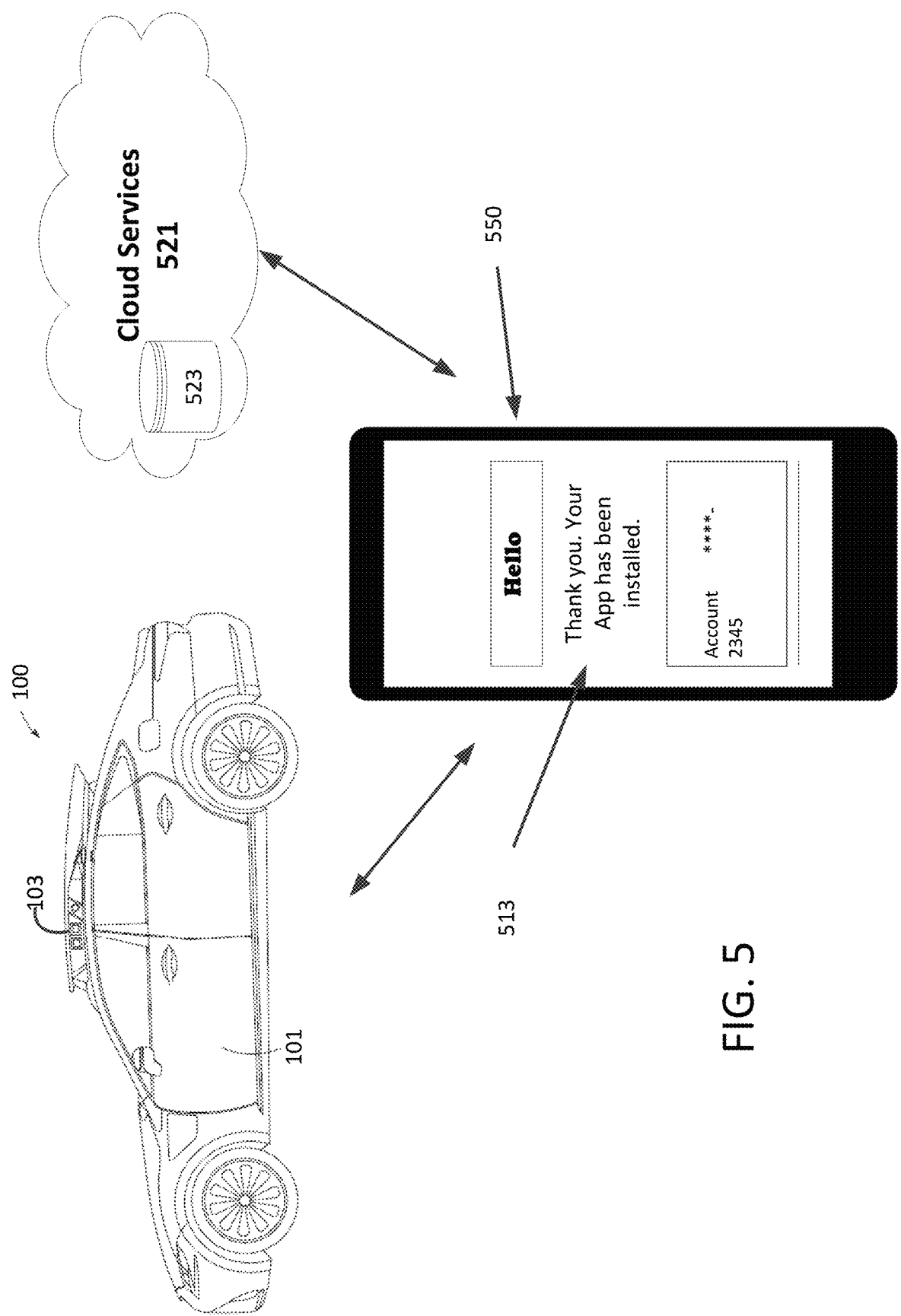
FIG. 5 is a system diagram of a medication monitoring app in accordance with an exemplary aspect of the disclosure.

FIG. 5 is a system diagram of a medication monitoring app in accordance with an exemplary aspect of the disclosure. In some embodiments, a medication monitoring mobile application 513, or app, may be installed in a mobile display device 550, such as a smartphone, tablet, or other wireless device having a display or audible function, or both. The mobile application 513 may be in communication with the HMI 341 of the vehicle 100. The mobile application 513 may utilize cloud services 521, including access to a database 523. In some embodiments, the vehicle 100 may include an inter-vehicle communication function to communicate with other vehicles, such as to exchange traffic conditions.

Upon installation of a mobile application 513, the mobile display device 550 may be sent a message that indicates that an account has been set up for use of the mobile application 513. The mobile display device 550 may display an indication that the mobile application 513 has been installed.

Figure 6:
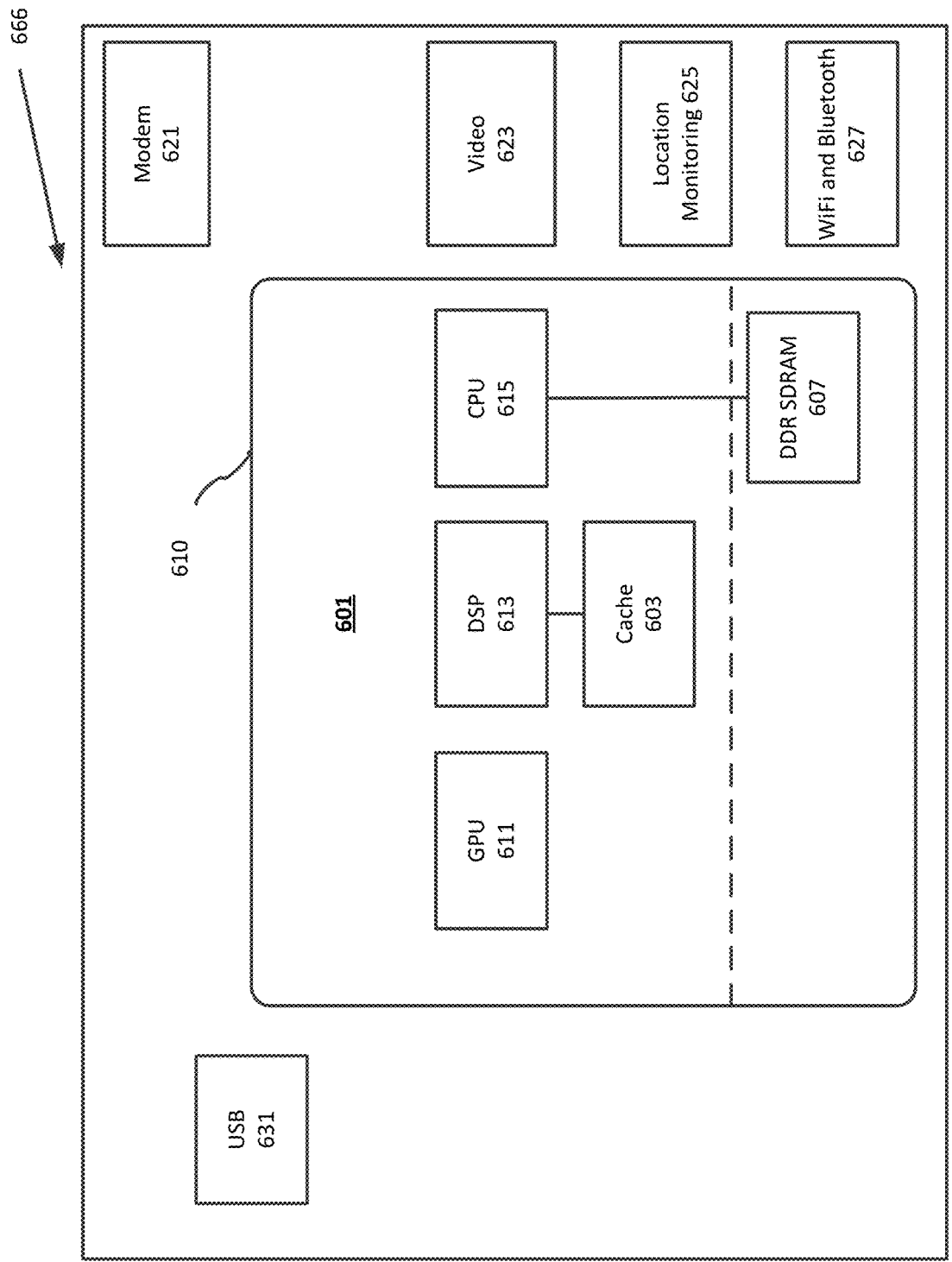
FIG. 6 is a block diagram of a computer system for a mobile display device.

FIG. 6 is a block diagram of a display processing system for the mobile display device in accordance with an exemplary aspect of the disclosure. In particular, FIG. 6 is a block diagram of a mobile display device 550. The display processing system 666 provides support for simultaneous camera sensor inputs, video decoding and playback, location services, wireless communications, and cellular services. The display processing system 601 includes a central processing unit (CPU) 615, and may include a graphics processing unit (GPU) 611 and a digital signal processor (DSP) 613. The CPU 615 may include a memory, which may be any of several types of volatile memory 607, including RAM, SDRAM, DDR SDRAM, to name a few. The DSP 613 may include one or more dedicated caches 603 in order to perform computer vision functions as well as machine learning functions. The GPU 611 performs graphics processing for a 4K resolution display device. The GPU 611, DSP 613, CPU 615, Cache 603, and in some embodiments, a cellular modem 621, may all be contained in a single system-on-chip (SOC) 601. The display processing system 666 may also include video processing circuitry 623 for video decoding and playback, location service circuitry, including GPS and dead reckoning, and connectivity service circuitry, including WiFi and Bluetooth. The display processing system 666 may include one or more input/output ports, including USB connector(s), such as connectors for USB 2, USB 3, etc.

Figure 7:
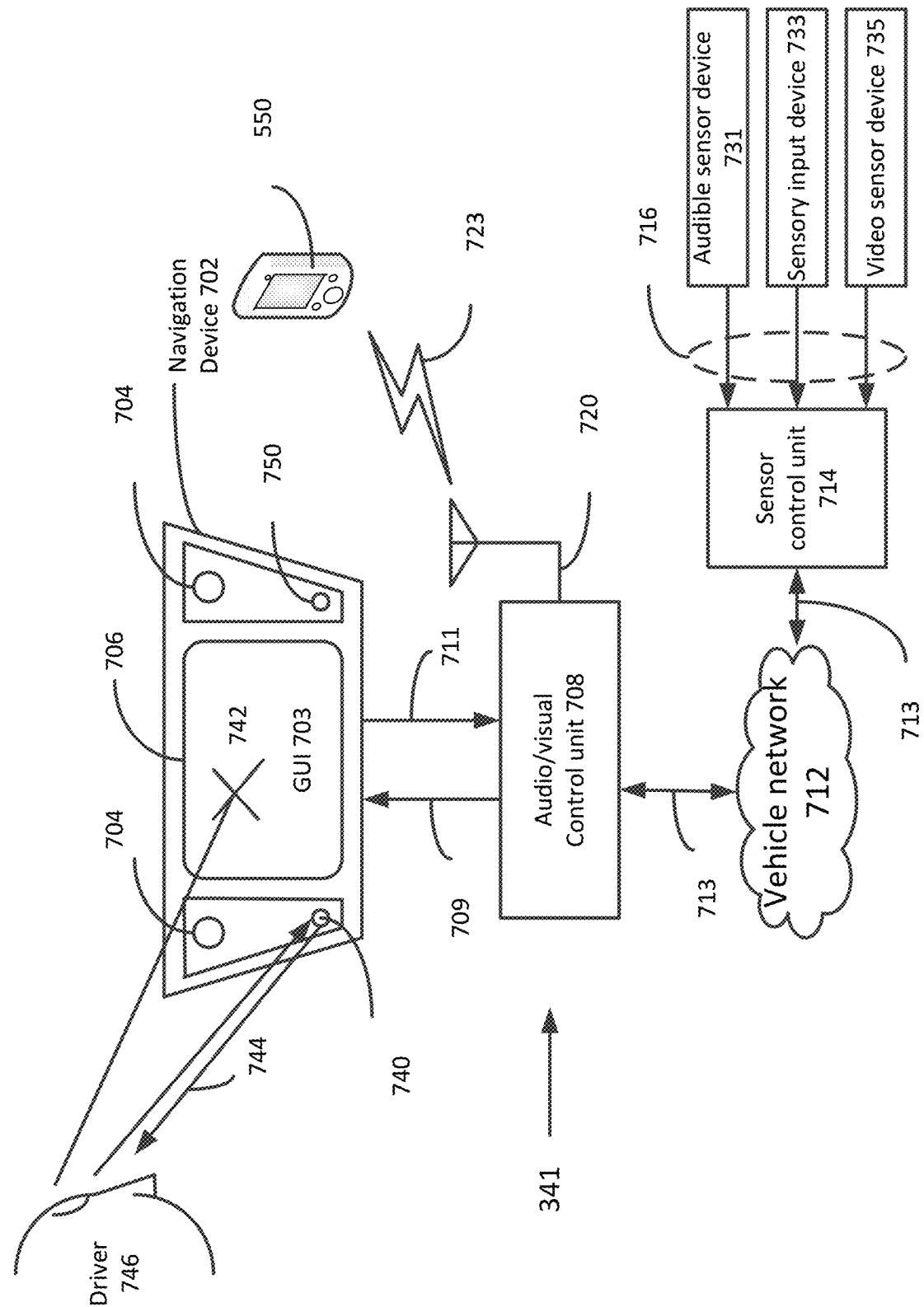
FIG. 7 is a schematic diagram of a human computer interface in accordance with an exemplary aspect of the disclosure.

In some embodiments, the mobile application 513 may synchronize (sync) with a navigation system, infotainment system, of the in-vehicle human machine interface system 341, and may communicate instructions/commands to the vehicle via the in-vehicle human machine interface system 341. FIG. 7 is a schematic diagram of a human machine interface in accordance with an exemplary aspect of the disclosure. While the human machine interface 341 is depicted in abstract with other vehicular components, the human machine interface 341 may be integrated with other system components of the vehicle 100 (see FIG. 2).

As shown in the example of FIG. 7, a vehicle navigation device 702 communicates through audio/visual control unit 708, which communicates with a sensor control unit 714 over a communication path 713 via vehicle network cloud 712.

As may be appreciated, the communication path 713 of the vehicle network 712 may be formed of a medium suitable for transmitting a signal such as, for example, conductive wires, conductive traces, optical waveguides, or the like. Moreover, the communication path 713 can be formed from a combination of mediums capable of transmitting signals. In one embodiment, the communication path 713 can comprise a combination of conductive traces, conductive wires, connectors, and buses that cooperate to permit the transmission of electrical data signals to components such as processors, memories, sensors, input devices, output devices, and communication devices. Accordingly, the communication path 713 may be provided by a vehicle bus, or combinations thereof, such as for example, a Body Electronic Area Network (BEAN), a Controller Area Network (CAN) bus configuration, an Audio Visual Communication-Local Area Network (AVC-LAN) configuration, a Local Interconnect Network (LIN) configuration, a Vehicle Area Network (VAN) bus, and/or other combinations of additional communication-system architectures to provide communications between devices and systems of the vehicle.

The term "signal" relates to a waveform (e.g., electrical, optical, magnetic, mechanical or electromagnetic), such as DC, AC, sinusoidal-wave, triangular-wave, square-wave, vibration, and the like, capable of traveling through at least some of the mediums described herein.

The sensor control unit 714 receives sensor data 716 from the audible sensor device 721, sensory input device 723, and video sensor device 725. For further example, the sensor data 716 operates to permit object detection external to the vehicle, such as other vehicles (including vehicles occupying a parking location), roadway obstacles, traffic signals, signs, trees, etc. The sensor data 716 allows the vehicle 100 (see FIG. 2) to assess its environment in order to maximize safety for vehicle passengers and objects and/or people in the environment. The sensor data 716 also provides information relating to a moving target, and to provide moving target indication (MTI) data.

As an example, the sensory input device 723 provides tactile or relational changes in the ambient conditions of the vehicle, such as an approaching person, object, vehicle, etc. The one or more of the sensory input devices 204 can be configured to capture changes in velocity, acceleration, and/or distance to objects relative to the travel of the vehicle 100, as well as an angle of approach. The sensory input devices 733 may be provided by a Light Detection and Ranging (LIDAR) system and/or milliwave radar devices. As an example, the sensory input devices 733 may identify objects in the roadway (such as other vehicle, debris, etc.), and may identify moving objects adjacent the roadway that may present a hazard to the vehicle 100 (such as animals and/or debris coming within the roadway).

Sensor data 716 relating to the video sensor devices 311 (see FIG. 3) operate to capture still-frame of and/or video images within associated fields of view for display to the touch screen 706 of the vehicle navigation device 702.

The audio/visual control unit 708 receives the sensor data 716 via the communication path 713 and vehicle network 712, and produces display data 709 for display by the touch screen 706. The audio/visual control unit 708 also receives user input data 711 from the vehicle navigation device 702, which may be from the tactile input 704, microphone 750, eye-tracking input device 740, etc.

The audio/visual control unit 808 may include an antenna 720 for wireless communications 723 with user devices, such as a mobile device 550.

The mobile device 550, by way of example, may be a device including hardware (for example, chipsets, processors, memory, etc.) for communicatively coupling with a network cloud and/or directly with the audio/visual control unit 708 via the antenna 720, and also includes an antenna for such wireless communication.

The antenna 720 may include one or more conductive elements that interact with electromagnetic signals transmitted by global positioning system satellites. The received signals may be transformed into a data signal indicative of the location (for example, latitude and longitude positions), and further indicative of the positioning of the device 550 with respect a vehicle position, that can be indicated on a map displayed via the touch screen 706, or otherwise displayed via the vehicle GUI 703.

The wireless communications 723 may be based on one or many wireless communication system specifications. For example, wireless communication systems may operate in accordance with one or more standards specifications including, but not limited to, 3GPP (3rd Generation Partnership Project), 4GPP (4th Generation Partnership Project), 5GPP (5th Generation Partnership Project), LTE (long term evolution), LTE Advanced, RFID, IEEE 802.11, Bluetooth, Bluetooth low energy, AMPS (advanced mobile phone services), digital AMPS, GSM (global system for mobile communications), CDMA (code division multiple access), LMDS (local multi-point distribution systems), MMDS (multi-channel-multi-point distribution systems), IrDA, Wireless USB, Z-Wave, ZigBee, and/or variations thereof.

The vehicle navigation device 702 includes, for example, tactile input 704, a touch screen 706, microphone 750, and eye-tracking input device 740. The touch screen 706 operates to provide visual output or graphic user interfaces such as, for example, maps, navigation, entertainment, information, infotainment, and/or combinations thereof.

The touch screen 706 may include mediums capable of transmitting an optical and/or visual output such as, for example, a cathode ray tube, light emitting diodes, a liquid crystal display, a plasma display, etc. Moreover, the touch screen 706 may, in addition to providing visual information, detect the presence and location of a tactile input upon a surface of or adjacent to the display. Accordingly, the display may receive mechanical input directly upon the visual output provided by the touch screen 706. Additionally, it is noted that the touch screen 706 can include at least one or more processors and one or more memory modules.

The vehicle navigation device 702 may also include tactile input and/or control inputs such that the communication path 713 communicatively couples the tactile input to other control units and/or modules of the vehicle 100 (see FIG. 2). The tactile input data may be provided by devices capable of transforming mechanical, optical, or electrical signals into a data signal capable of being transmitted via the communication path 713.

The tactile input 704 may include a number of movable objects that each transform physical motion into a data signal that can be transmitted over the communication path 713 such as, for example, a button, a switch, a knob, etc.

The touch screen 706 and the tactile input 704 may be combined as a single module, and may operate as an audio head unit or an infotainment system of the vehicle 100. The touch screen 706 and the tactile input 704 can be separate from one another and operate as a single module by exchanging signals.

Touch screen 706 may include a display screen, such as a liquid crystal display (LCD), light emitting diode (LED), plasma display or other two dimensional or three dimensional display that displays graphics, text or video in either monochrome or color in response to display data 709.

A built-in eye-tracking input device 740 includes a near-infrared light transmitter that projects a pattern of tracking signals 744 onto the eyes of the user 746. The built-in eye-tracking input device 740 also includes a camera operable to take high-frame-rate images via the tracking signals 744 of the user's eyes and the reflected patterns. In this manner, the built-in eye-tracking input device 740 operates to determine a gaze point 742 of the touch screen 706. As with a physical touch of the touch screen 706, the gaze point 742 may be used as a user input, which is provided as user input data 711 to the audio/visual control unit 708.

Figure 8:
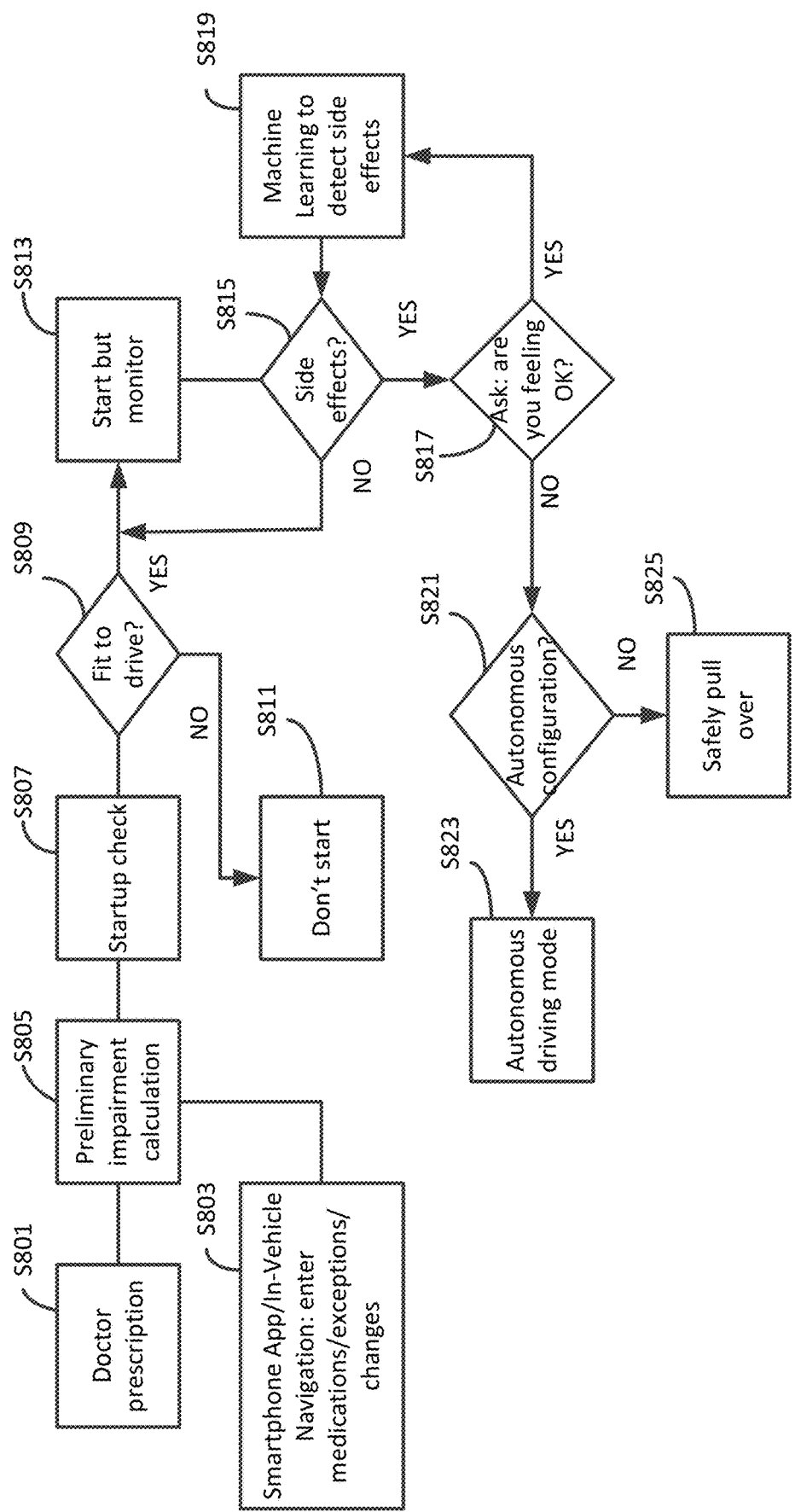
FIG. 8 is a flowchart for a method of predictive impairment monitoring in accordance with an exemplary aspect of the disclosure.

FIG. 8 is a flowchart for a method of predictive impairment monitoring in accordance with an exemplary aspect of the disclosure. Regarding FIG. 8, a mobile app 513 or vehicle driver monitor system 300 may perform a check as to whether the driver is fit to drive a vehicle before the vehicle is started. Medications that a driver is taking may be obtained, in S801, from a doctor prescription or an electronic medical record. Other medications that are taken occasionally may be entered, in S803, through the mobile app 513 or vehicle driver monitor system 300. For example, a driver may take an occasional medication such as melatonin to help sleep or an antihistamine for minor allergies. Although taking occasional medications like sleep medications and antihistamines have relatively short half-lives on the order of about one hour and may have fewer side effects, a driver may alter a dosage or take a medication that may cause side effects such as dizziness or daytime sleepiness. For example, taking a dosage of melatonin that is greater than the proper dose of 1 to 5 mg can disrupt a person's circadian rhythm and cause daytime sleepiness. The occasional medications may be entered by capturing an image of the medication label with the camera of the smartphone using the mobile app 513.

Figure 9:
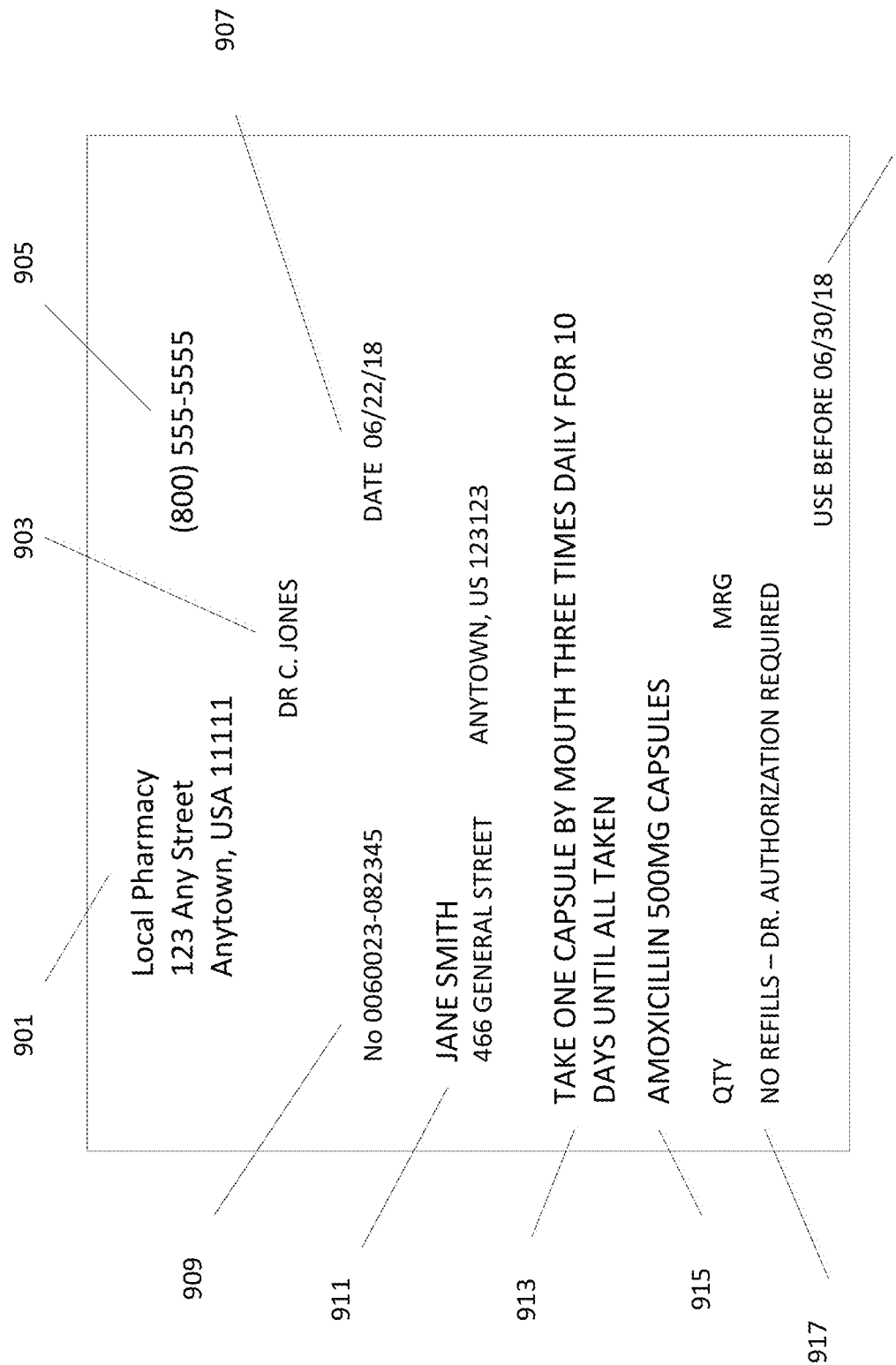
FIG. 9 is a medication label for an exemplary prescription drug.

FIG. 9 is a medication label for an exemplary prescription drug. By capturing an image of a label of a prescription drug, information about the medication such as the drug name and strength, when and how often the drug is to be taken may be obtained. The exemplary medication label may include a name and address of the pharmacy 901, the doctor's name 903, a drugstore phone number 905, a prescription file date 907, an identifier used by the drugstore for refills, the patient name 911, instructions about how often and when to take the drug 913, name of drug and strength of drug 915, number of refills 917, and a use-by date 919.

Figure 10:
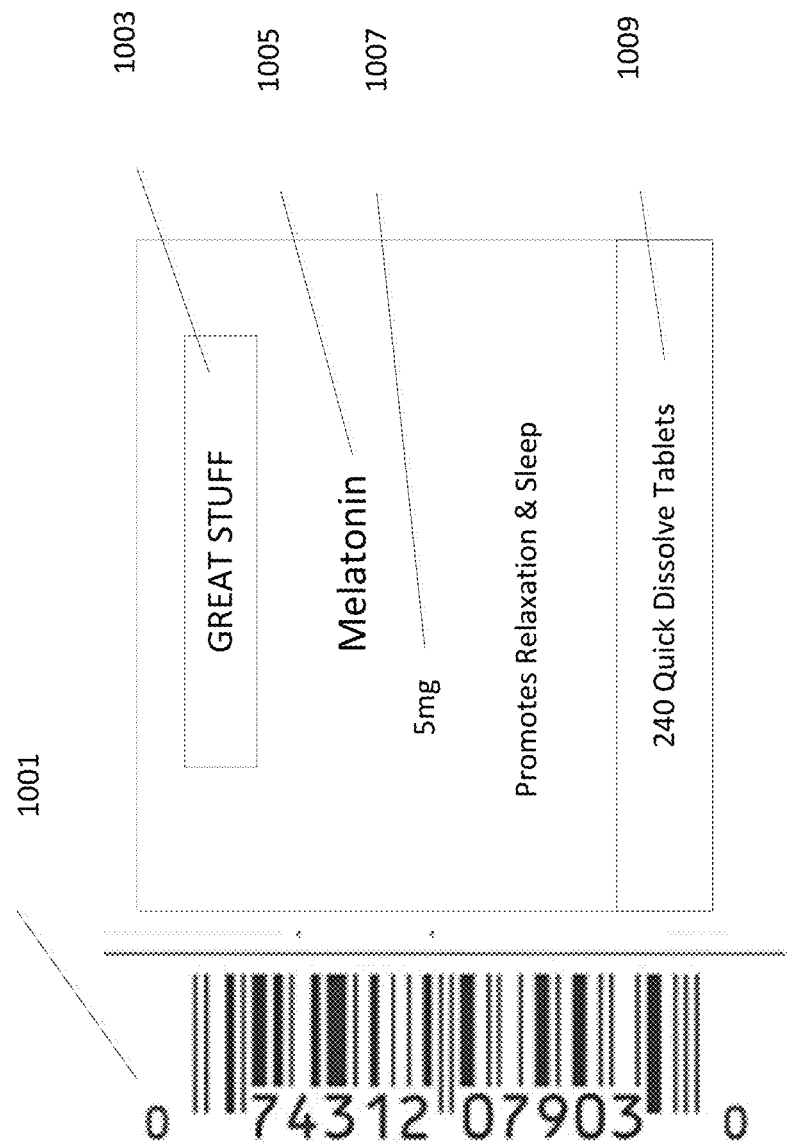
FIG. 10 is a mediation label for an exemplary over-the-counter medication.

FIG. 10 is a mediation label for an exemplary over-the-counter medication. Similar to a prescription drug, the name and strength of the medication may be obtained by capturing an image of the medication label. A label for an over-the-counter medication may vary depending on the drug manufacturer. FIG. 10 is an exemplary medication label that may be captured by a camera in the case of a manufacturer's label. A manufacturer's label may include the brand name 1003, a drug name 1005, the strength of the drug 1007, the contents 1009 of the package. The package may be identified by a universal product code number and an associated barcode 1001. The universal product code includes the manufacturer's identification number and the product number. The universal product code may be used to obtain further information about the product from a database.

Figure 11:
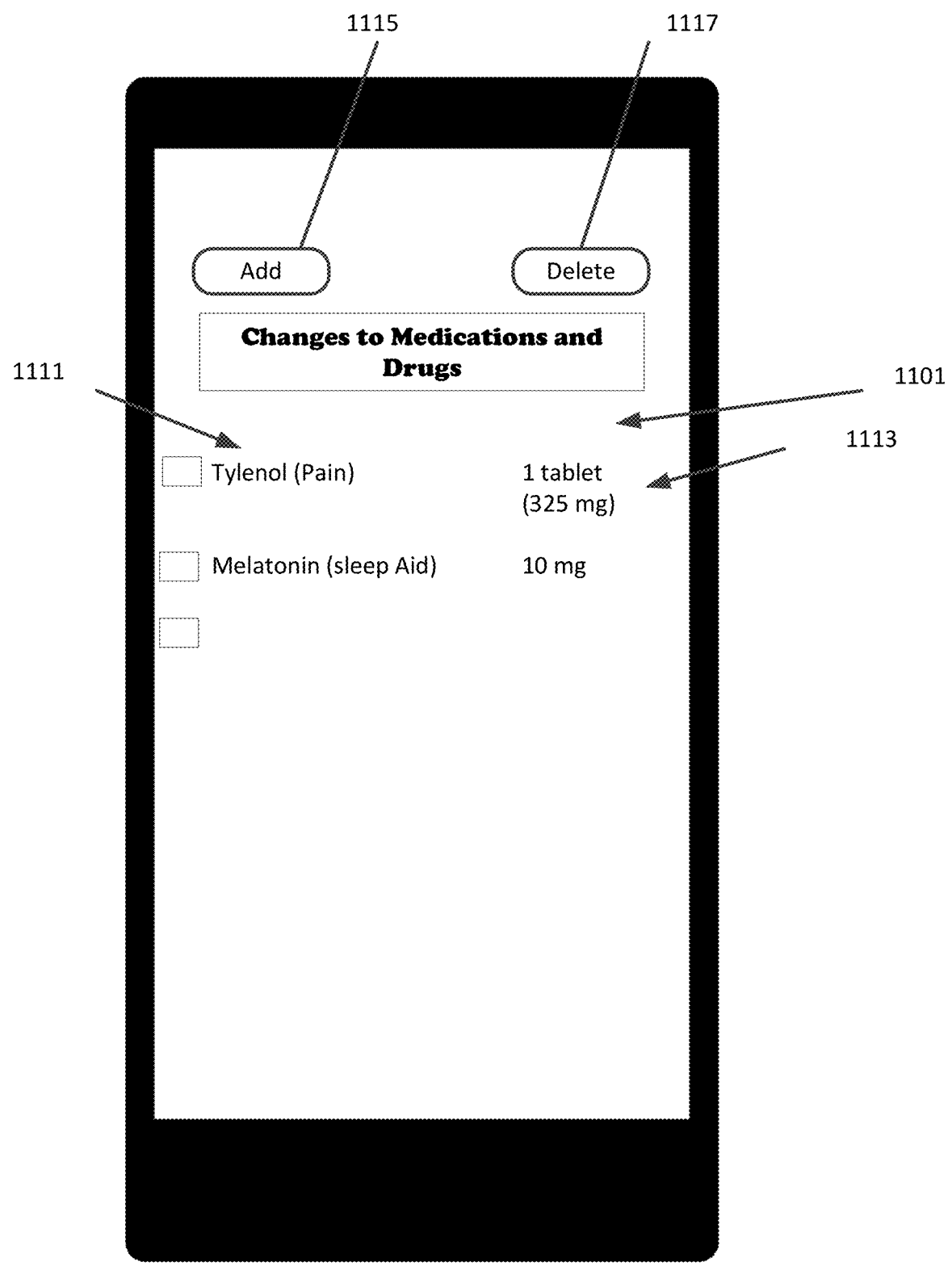
FIG. 11 is a display for a medication monitoring app for creating a list of medications in accordance with an exemplary aspect of the disclosure.

In some embodiments, a list of medications that are being taken may be entered manually or extracted from an image of a medication label to supplement medications that are obtained from medical records. FIG. 11 is a display for a medication monitoring app for creating a list of medications in accordance with an exemplary aspect of the disclosure. In a mobile application 513 for monitoring medications with respect to a driver of a vehicle, the mobile application 513 may be provided with a user interface screen for adding or deleting from a list of one or more medications 1111 being taken by the patient/driver. It is preferred that the list include the strength 513 of each medication. The mobile application 513 may include a form for manual entry of medications, where the added medications may be entered by using a camera function of the mobile device 550. The camera of the mobile device 550 may be used to capture an image of a product label on the container of a medication. The mobile application 513 may perform optical character recognition (OCR) to extract information of the medication from the image of the product label. The mobile application 513 may extract a product ID, which may be used to obtain the name of the medication and dosage amount from a database, such as a database 523 maintained in the cloud services.

The database 523 may be a relational database or a table in a flat file depending on the size of the database. A table in a flat file may be used when the database is for an individual patient driver, whereas a relational database or some other database system may be used for a database of general medication information. The medication list of an individual patient itself may be maintained in a table. Such a table may be stored locally in the mobile device 550.

A database 523 of general medication information may include an ID that is unique to a product in a particular container (e.g., a drugstore, manufacturer ID), or may be an ID established by the database that identifies the product (for example, an ID that is unique to the product, including the product name, form—tablet, gel, etc., quantity—100 tablets, etc., strength). Other information identifying the medication contained in the database 523 may include the product name, generic drug name, strength, prescription fill date or a purchase date, a product expiration date. The database 523 may contain additional information about medications such as instructions about how often and when a drug is to be taken and the class of the medication such as antidepressants, benzodiazepines, sleep medications, etc.

The database 523 may contain a half-life of a medication. The half-life of a drug is a pharmacokinetic parameter that may be defined as the time it takes for the concentration of the drug in the plasma or the total amount in the body to be reduced by 50%. In other words, after one half-life, the concentration of the drug in the body will be half of the starting dose. As an example, if 100 mg of a drug with a half-life of 60 minutes is taken, then 60 minutes after administration, 50 mg remains, after 120 minutes after administration, 25 mg remains, and after 180 minutes, etc.

Also, the drug half-life varies for each person. The drug half-life can vary based on several factors including a person's weight, gender, age, blood circulation, diet, fluid levels (excessive or dehydrated), history of previous drug use, kidney function, liver function, obesity, pre-existing conditions (heart failure, gastrointestinal disorders), presence of drugs that compete for binding sites or interact, race/ethnicity, smoking, and other factors.

For purposes of this disclosure, the half-life of a medication that is stored in the database 523 is a generic half-life of the medication that may be adjusted based on a person's weight.

The displayed list of medications may include a function to add a medication, for example in the form of a button 1115, and a function to delete a medication, for example in the form of button 1117. A function may also be included to edit the list of medications, such as in the case that a dosage amount of a medication is changed or in the case that the name of the medication has changed. As indicated above, a medication may be added to the list using the camera function of the mobile device 550. When a medication is to be added using the mobile application 513, the mobile application 513 may check a database 523 of medications in the cloud services 521 for similar medication products, and/or medication products that should not be combined with the medication to be added. The information retrieved from the database 523 may be used by the mobile application 513 to determine if there may be other medications in the list of medications that may be redundant medications (i.e., providing an increased dosage of the same or similar drug), or if there are medications in the list that should not be taken together with an added medication. The mobile application 513 may include a function to generate a report of possible multiple medications and possible drug interaction issues, and display the report. In some embodiments, the redundant medications and drug interaction issues may be well known information that is used to check the list of medications 1111.

Figure 12:
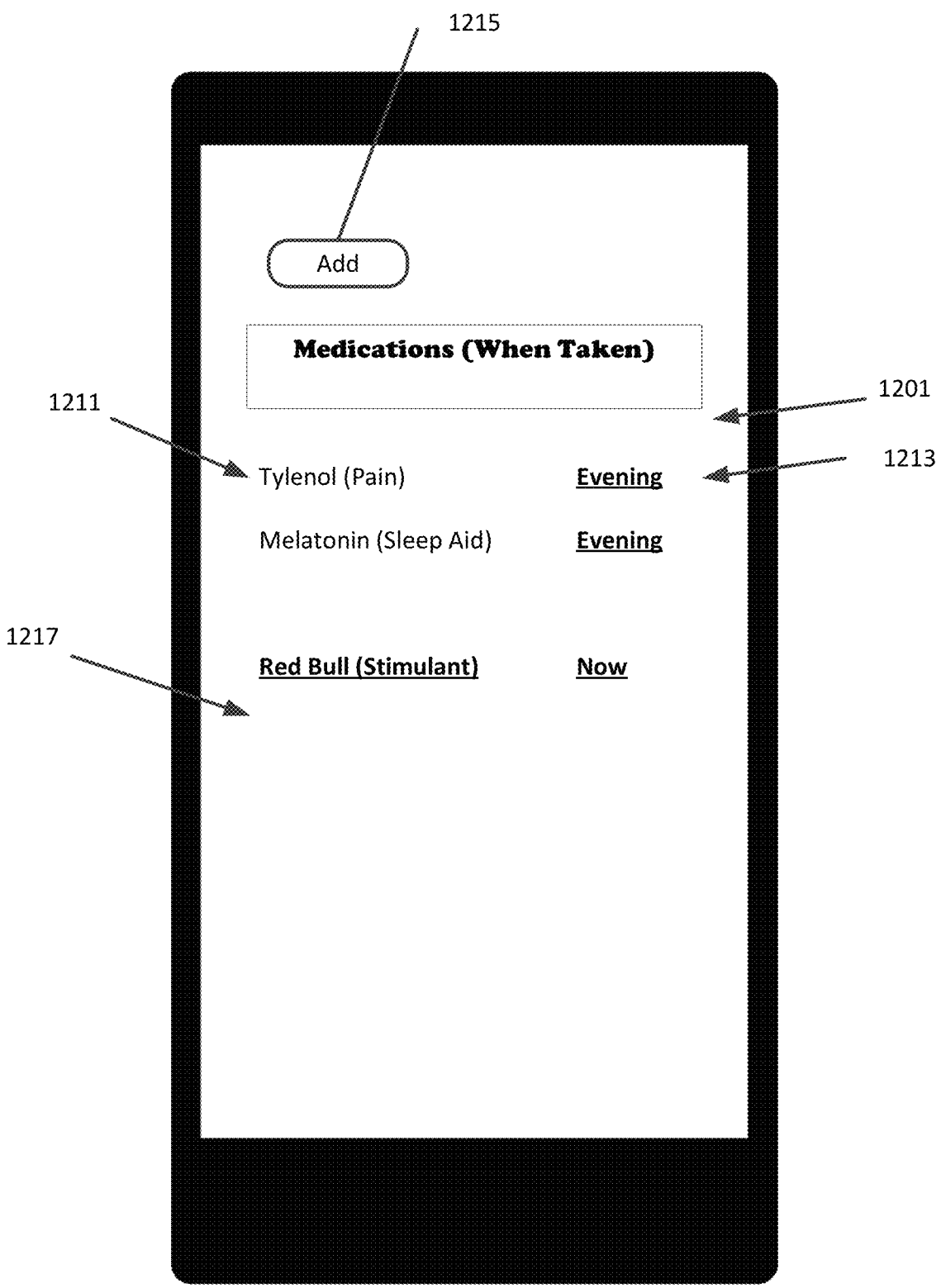
FIG. 12 is a display for a medication monitoring app for entry of medication status in accordance with an exemplary aspect of the disclosure.

FIG. 12 is a display for a medication monitoring app for entry of medication status in accordance with an exemplary aspect of the disclosure. In some embodiments, a driver may pull up the mobile application 513 to display a screen for managing status of medications taken. The status display may allow for entry of a time, or time of day, 1213 that a medication 1211 in the previously entered medication list 1211 is taken. In some embodiments, the status of a medication may be updated by a function that detects the time and date that is maintained in the mobile device 550. The updating of the status may be by way of clicking on listed medications as they are taken. In addition, the driver may enter additional drug-related products 1115, especially those that contain caffeine or alcohol. In the example display screen, the driver has added a stimulant that is being consumed. The driver may also enter any over-the-counter products that have not already been entered in the original list of medications 1111. For example, the driver may have taken an over-the-counter allergy medication because they believe they are presently having allergy problems. The allergy medication may be non-drowsy type, or may be a drowsy type medication. Other nighttime medications, even if taken a night before driving, can be entered with their most recent time.

In S805, a preliminary impairment calculation may be performed in the mobile app 513 or driver monitor system 300 which takes into account the specific medication and an associated medication half-life. The preliminary impairment calculation may be based on the time of day, regularity, and dosage indicated on the medication prescription.

Figure 13:
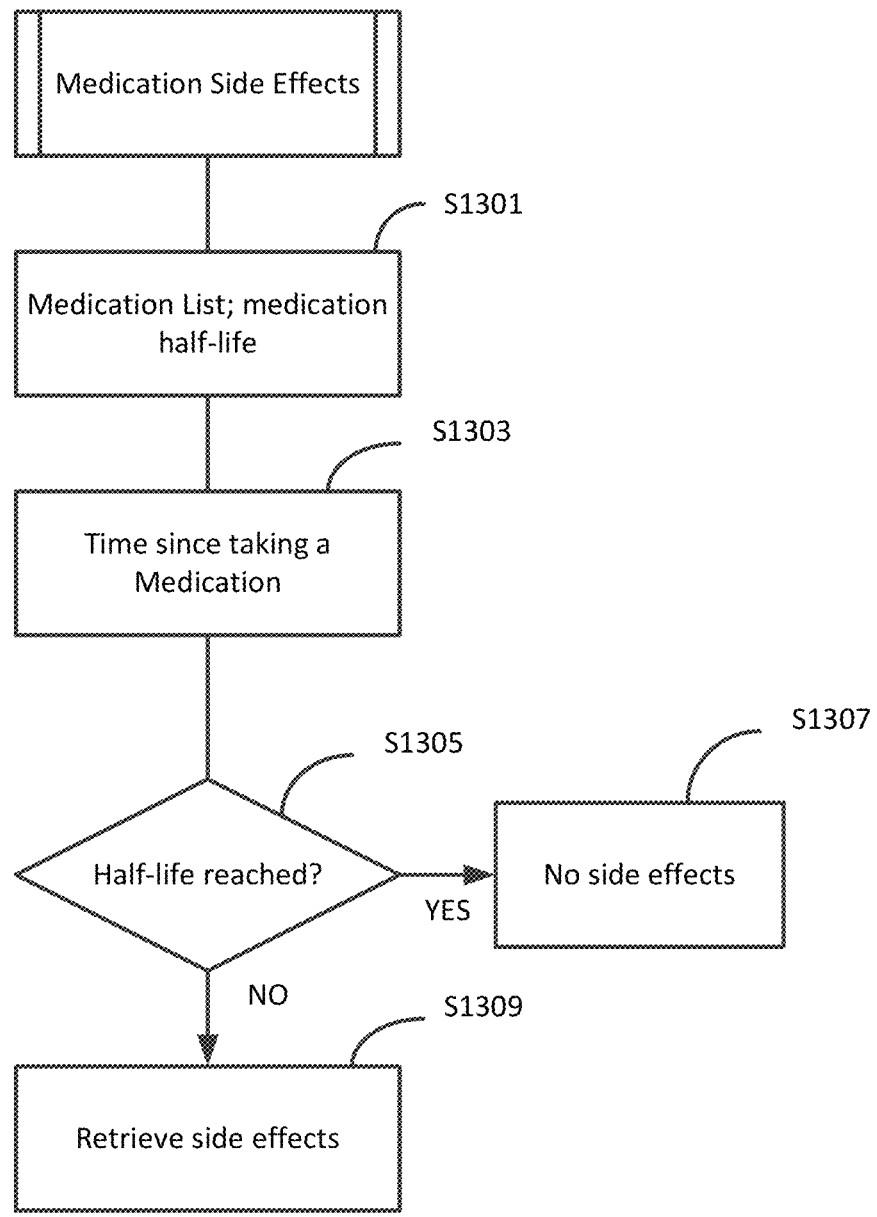
FIG. 13 is a flowchart of a method of evaluating medication side effects in accordance with an exemplary aspect of the disclosure.

FIG. 13 is a flowchart of a method of evaluating medication side effects in accordance with an exemplary aspect of the disclosure. The preliminary impairment calculation, S805, may be determined based on a time since a medication is taken and utilizes the medication half-life. In S1301, the medications that a driver is taking are retrieved from the database 523 based on those input in the mobile application 513, such as using the screen shown in FIG. 5 and any additional medications entered when the medication status screen 1101, such as in FIG. 11, is displayed. Medication names may be the name of the drug and/or may be a generic drug name. In some cases a medication name may just be a drug class depending on what is known about the medication. A strength 513 of medication is associated with the medication name in the medication list 1111 and is also retrieved from the database 523. In addition, the half-life of each medication is retrieved from the database 523 based on the medication name.

When medication side effects are determined, the current time is obtained. The current time may be obtained from the mobile device 550 or from some other accurate time source. Also, the time that each medication is taken may be obtained based on input in the status screen 1101, such as in FIG. 11. In S1303, the period of time since taking a medication is determined using the time that each medication is taken. In S1305, a decision is made as to whether the half-life of each medication is reached?

In some embodiments, the medication side effects are stored in the database 523. The side effects of a medication are considered maximum when the medication is first taken, but are calculated as a reduced effect based on the medication half-life. Side effects may be considered as being safe levels after the half-life of a medication. For example, if a medication half-life is one hour, a side effect of drowsiness may be considered to be sufficiently alleviated such that it would be safe to drive after one hour.

When the half-life of each medication in the list of medications has been reached (YES in S1305), in S1307, the mobile application 513 outputs that there are no side effects from medications. When the half-life of at least one medication in the list of medications has not been reached (NO in S1305), in S1309, side effects for the at least one medications are retrieved from the database 523.

Figure 14:
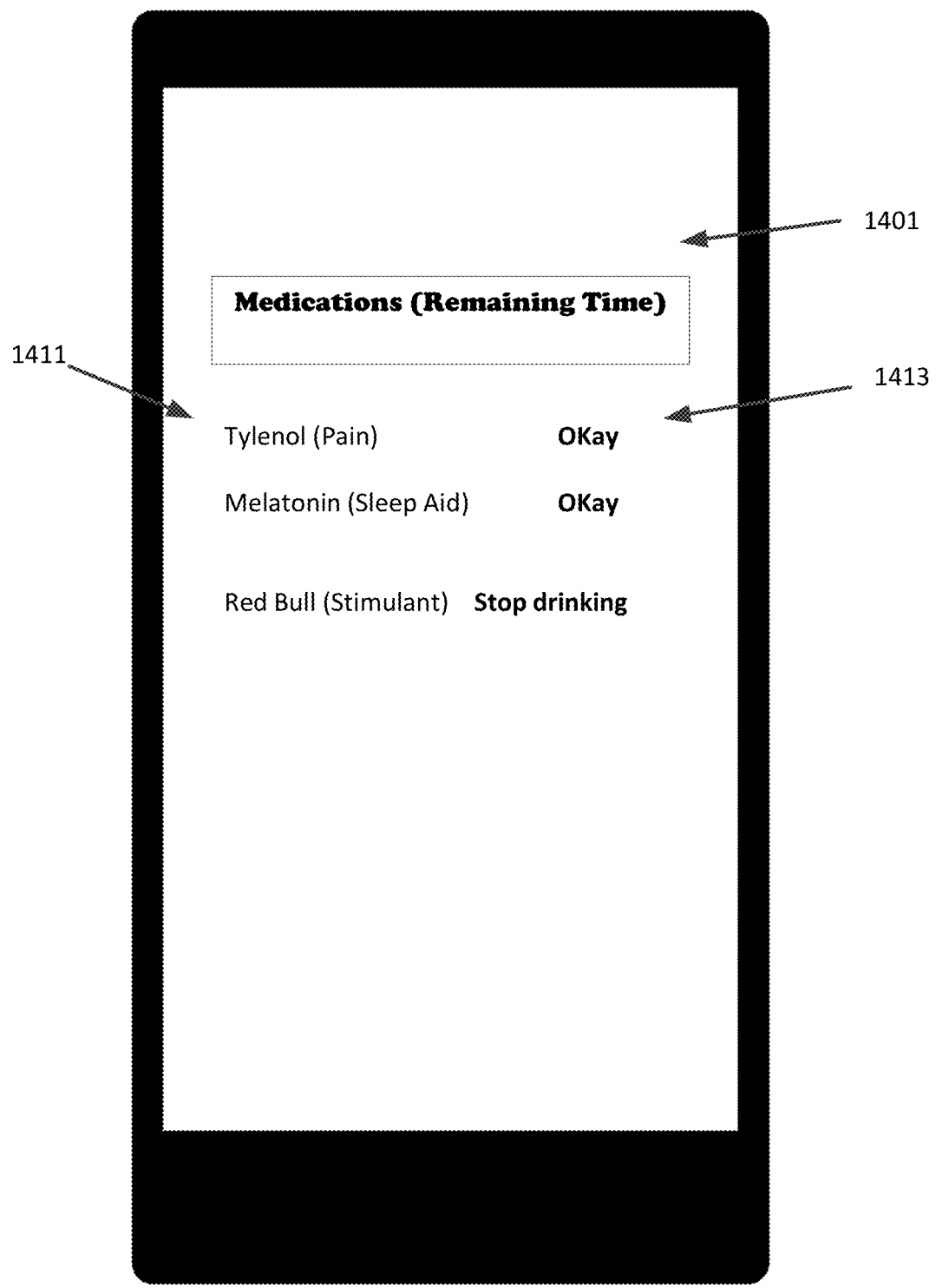
FIG. 14 is a display for a medication monitoring app for notifying a driver in accordance with an exemplary aspect of the disclosure.

In some embodiments, the mobile application may display a result of the preliminary impairment calculation. FIG. 14 is a display for a medication monitoring app for notifying a driver in accordance with an exemplary aspect of the disclosure. The mobile application 513 may use the results of the preliminary impairment calculation to make a prediction as to whether it would be safe for a driver to drive a vehicle at a current time. The mobile application 513 may make the prediction based on processing performed in the cloud services 521, or may make the prediction in the mobile device 550 itself, or may even use computer resources of the vehicle 100. FIG. 14 is an example display 1401 of a notification message that has been prepared as a result of a prediction. The notification message may list 1411 the medications that have been used in the prediction and an indication 1413 of an impact that the medication may have on driving a vehicle. The impact may include a side effect(s) of taking the medication, whether or not it would be safe to drive, or a message concerning the medication taken. In the example display 1401, the mobile application 513 recommends to stop taking an energy drink as the energy drink may actually have an effect of further reducing cognitive concentration when taken together with the other medications. There may be other situations in which the mobile application 513 makes a prediction that it would be unsafe to drive a vehicle based on the dosage amount and timing of taking a medication. The mobile application 513 may instruct the vehicle 100 to take action, such as switch to a higher level of driver assistance, prevent the vehicle from being started, take over control of certain vehicle operations, depending on the predicted state of the driver and the driver assist features that a vehicle is equipped with.

Figure 15:
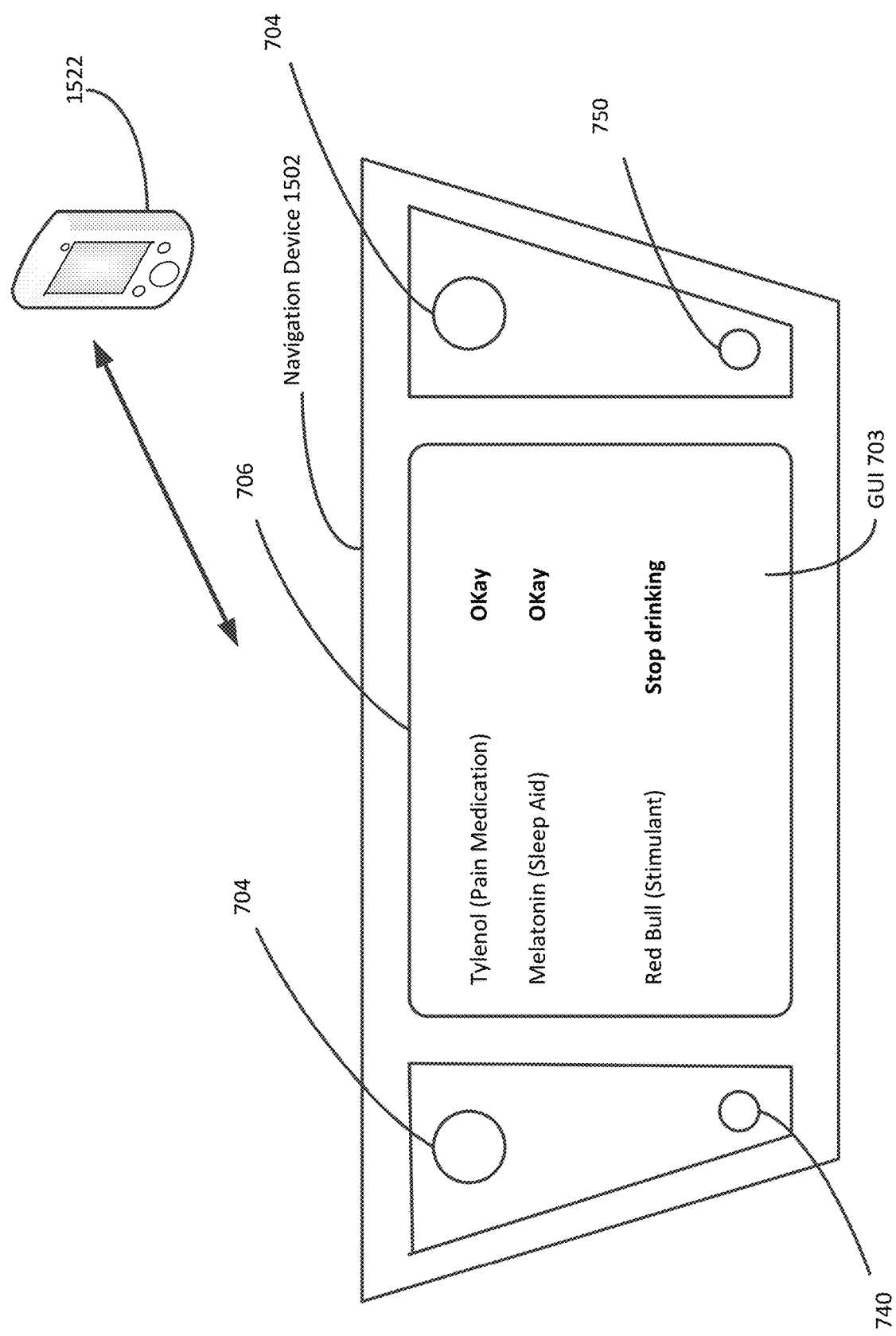
FIG. 15 is a display for an in-vehicle navigation display device in accordance with an exemplary aspect of the disclosure.

FIG. 15 is a display for an in-vehicle navigation display device in accordance with an exemplary aspect of the disclosure. The mobile device 550 may synchronize with a display device of the vehicle 100 and may communicate instructions/commands to an in-vehicle computer system. FIG. 15 is an example display in a case where the mobile device 550 is in synchronization with the in-vehicle navigation display device 1502. The information that is displayed may be substantially the same as the information displayed for the mobile device 550, as in FIG. 14 for example.

In S807, a startup check is performed which may involve a dual check that includes both a physical check and a questionnaire.

Figures 16A, 16B:
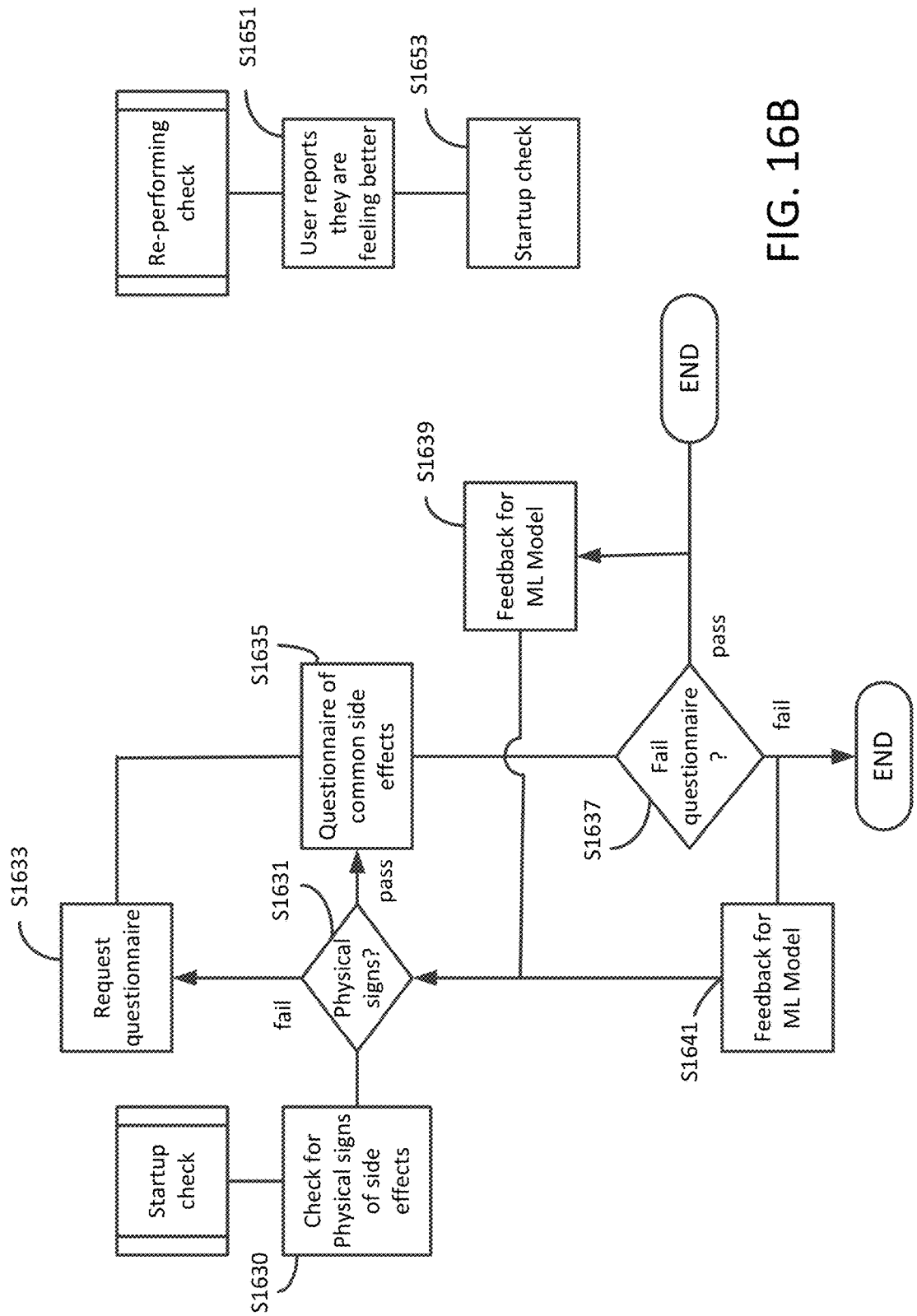
FIGS. 16A, 16B is a flowchart of the startup check of FIG. 8.
Figure 17:
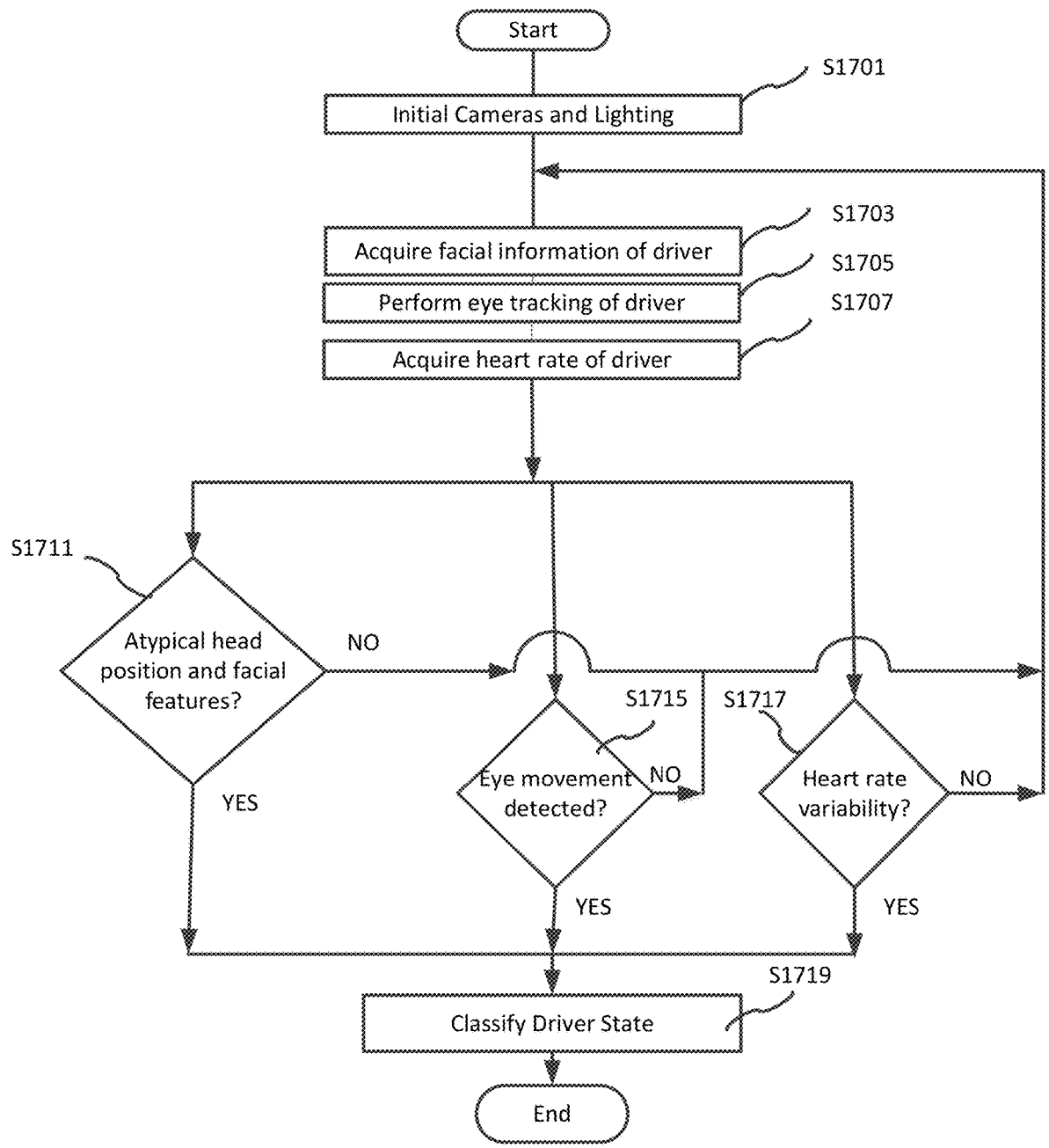
FIG. 17 is a flowchart of a method of driver monitoring in accordance with an exemplary aspect of the disclosure.

FIGS. 16A, 16B is a flowchart of the startup check of FIG. 8. In S1630, the driver monitor system may be used to check for physical signs of side effects. Physical signs of drowsiness FIG. 17 is a flowchart for determining a driver state in accordance with an exemplary aspect of the disclosure. A driver monitor system may be initially set up off line for a driver or drivers of a vehicle. The driver or drivers may enter into a user interface information about the driver, which may include creating a driver behavior profile.

When a driver enters a vehicle and sits in the driver's seat, in S1701, the ECU 105 may turn on certain sensors, including heart rate monitor sensors 317, in-cabin cameras 311 and light sources 313. In some embodiments, initial sensors 311, 315, 317 and light sources 313 may be turned on when the engine is started. In some embodiments, all interior cabin sensors may be turned on. In some embodiments, only a subset of in-cabin cameras 311 and light sources 313 may be turned on.

In S1703, the initial in-cabin cameras 311 and light sources 313 are used to acquire facial information of a driver. The driver's face may not be facing forward or may not be facing toward the initial in-cabin cameras 311. Additional or alternative in-cabin cameras 311 may be turned on in order to obtain an image of the driver's face. In addition to obtaining an image of a driver's face, particular features may be monitored such as facial blood flow, head position, body position, and yawning.

In S1705, at least one in-cabin camera 311 may be used for eye tracking of the driver. As mentioned above, eye tracking may include functions of monitoring eye movement and eye gaze direction, and in particular, saccade velocity, acceleration, and frequency, and duration of eye gaze.

In S1707, heart rate sensors may be used to provide the heart rate of the driver and in turn the heart rate information may be used to determine a heart rate variability pattern.

In S1711, the ECU 105 may detect a head position that may indicate sleepiness or may detect facial features that indicate yawning, anxiety or lack of concentration.

In S1715, the ECU 105 may detect that the driver's eyes have moved away from the forward direction to a left, right, or downward eye gaze direction for a predetermined period of time.

In S1717, the ECU 105 may detect that the driver's heart rate variability has changed by a predetermined amount. In some embodiments, the ECU 105 may detect that the driver's heart rate variability is below the resting heart rate variability for a predetermined period of time. The heart rate variability may be measured over a predetermined period of time, such as in a range of two to five minutes.

In S1719, provided results of atypical facial features, eye movement, and the heart rate variability, as well as head movement and position, body position, the ECU 105 may classify a driver's physical and mental state. In preferred embodiments, the driver's physical and mental state is normal, or one or more of conditions that are possible side effects of medications.

In S1631 of FIG. 16A, a decision is made as to whether the driver's physical and mental state is a side effect of a medication.

Machine learning may be used to predict whether a driver is moving into a side effect of a medication, such as a fatigue state, some other reduced cognitive state, or other side effect. The machine learning model may be made off line using a supervised learning algorithm, such as a Support Vector Machine (SVM) or regression analysis, or may be made by a continuous learning algorithm, such as reinforcement learning.

Figure 18A:
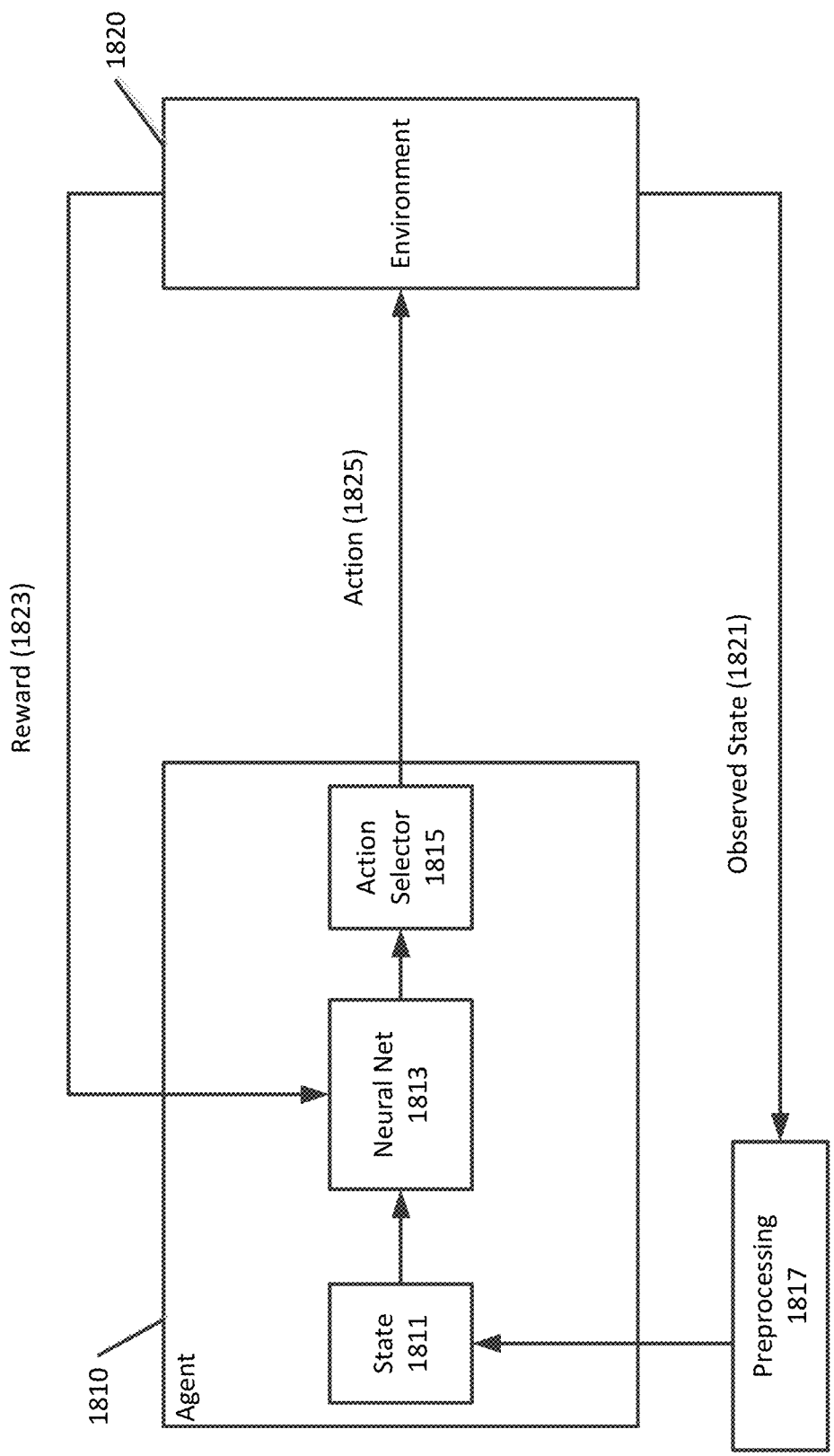
FIGS. 18A, 18B are a block diagram of a reinforcement learning system and an artificial neural network architecture in accordance with an exemplary aspect of the disclosure.
Figure 18B:
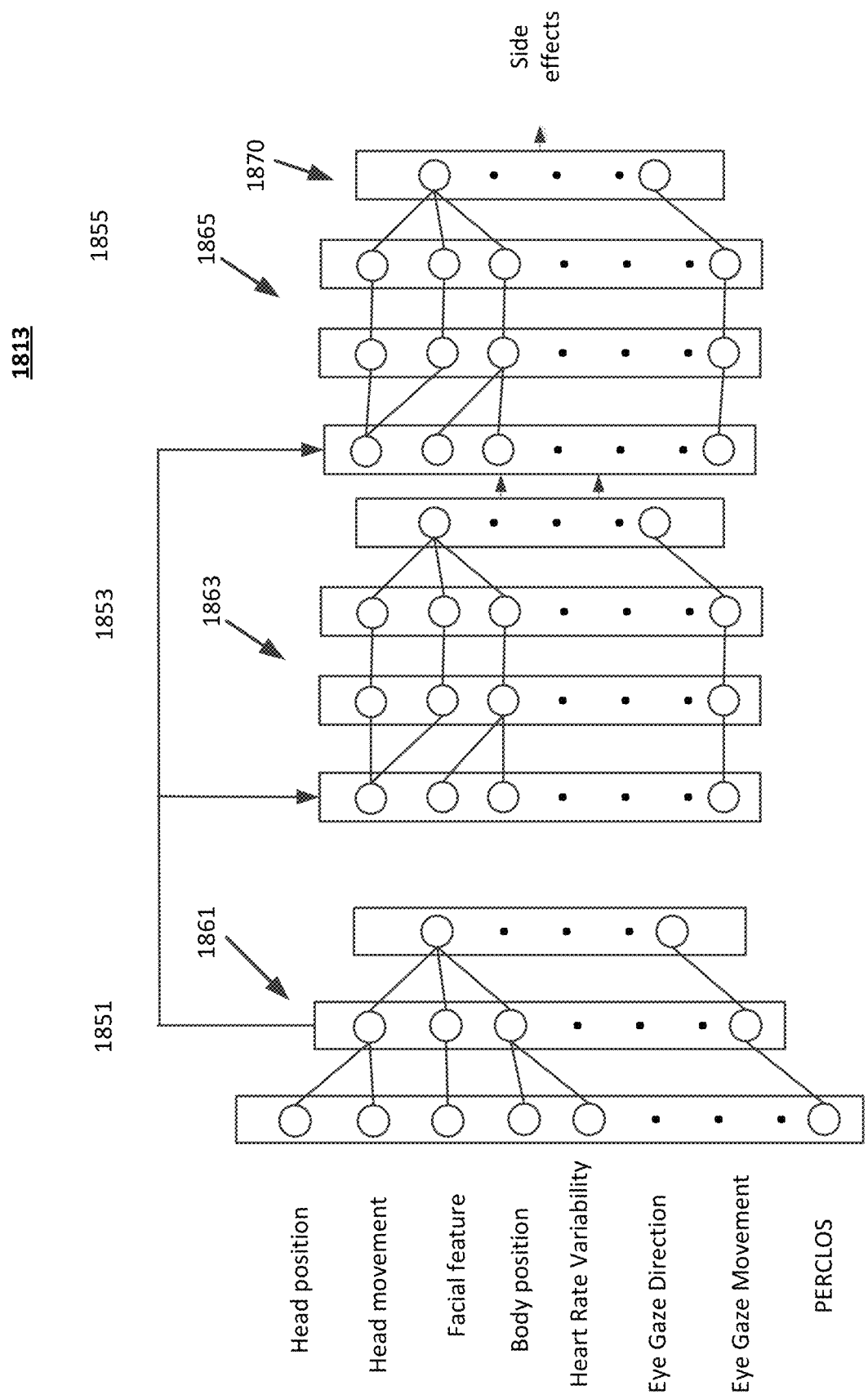

FIG. 18A is a block diagram of a reinforcement learning system in accordance with an exemplary aspect of the disclosure. FIG. 18B is an architecture for the artificial neural network of FIG. 18A.

In reinforcement learning, an agent 1810 interacts with an environment 1820 in discrete time steps. Learning is performed in an artificial neural network 1813. The artificial neural network 1813 may be a multi-layered network having at least one hidden layer. The input layer of the network 1813 is arranged according to a vector representation of the state 1811. The output layer of the network 1813 will consist of one neuron for each possible action. At each time t, the agent 1810 receives an observation which typically includes the reward. It then chooses 1815 an action from the set of available actions (output from the neural network 1813), which is subsequently sent to the environment 1820. The environment 1820 moves to a new state and the reward associated with the transition is determined. The goal of a reinforcement learning agent is to collect as much reward as possible. The agent 1810 can (possibly randomly) choose any action as a function of the history.

The driver monitor system 300 may include feedback input from the driver to train a machine learning algorithm. Reinforcement learning allows for continuous learning and may learn based on the driver feedback. The driver monitor system's 300 sensors (Observed state 1821) are fed to the artificial neural network 1813 which may detect a state of a driver. An action selector 1815 will select an action 1825, such as ask the driver, "Are you thinking about something intently right now?" for an out of focus state or "Are you feeling sleepy at this moment?" for fatigue. A positive reward 1823 (e.g., +1) will be awarded when the answer to the question is Yes. A negative reward 1823 (e.g., −1) may be awarded when the answer to the question is No, or Not at all. A lower positive reward (e.g., +0.5) may be awarded when the answer to the question is Somewhat. The driver monitor system 300 may perform preprocessing 1817 of sensor data, including quantifying the sensor data. For example, a 3-pt scale may be implemented (1—not at all, 2—somewhat, 3—yes) to help ordinate the sensor data. This data 1811 is then fed back into the artificial neural network 1813 so that the system is able to more effectively and rapidly detect driver states for that specific driver and issue an appropriate action.

FIG. 18B is a block diagram of the architecture for the artificial neural network in accordance with an exemplary aspect of the disclosure. The architecture of the artificial neural network 1813 may include an encoder 1851, and a sequence of N tandem decoders 1853, 1855. The encoder 1851 is a shallow artificial neural network with one hidden layer 1861. The encoder 1851 generates vector representations of the input driver state. In one embodiment, after training the encoder 1851, the hidden layer 1861 represents the vector representation for the driver state. Each decoder 1853, 1855 is a multilayer artificial neural network, each having at least two hidden layers 1863, 1865, 1867, i.e., is a deep learning neural network. Although FIG. 18B shows three artificial neural networks arranged as tandem decoders, the number of decoders may be different depending on desired accuracy and training time. A decoder 1853 takes the vector representations as inputs and outputs the driver class. During training, a subsequent decoder 1855 takes the vector representations as inputs and uses the outputs of the upstream decoder 1853 as targets. This method of training is performed in other downstream decoders in sequence. Each decoder 1853, 1855 may be an artificial neural network architecture that is trained using the backpropagation algorithm. An output layer 1870 of the last decoder outputs the actions based on a detected driver class.

The artificial neural network is trained by adjusting weighted connections between the layers. These weighted connections, or parameters, of the artificial neural network may be stored in the profile associated with a driver. In some embodiments, different drivers may have their own artificial neural network with associated parameters, which may be stored in independent profiles for each driver.

Each driver profile may include a resting HRV. A low HRV may be defined as an HRV that is below the resting HRV. A high HRV may be defined as an HRV that is above the resting HRV. This driver profile can be stored in a cloud-based database 523 and accessed by any vehicle with the medication monitoring mobile application 513.

As an alternative to reinforcement learning, a machine learning model may be determined using the driver profile and Support Vector Machines (SVM). A SVM is a binary classifier, meaning it classifies data samples into one of two classes. In the case of classifying a driver of being in a cognitive tunneling state, fatigue state, or some other state, the classification requires classifying the data into three or more classes, a problem referred to as multiclass classification. One strategy to solving the multiclass classification problem using binary classifiers is to train a single classifier for each class, known as one-vs-rest strategy. In the one-vs-rest strategy, each classifier produces a real-valued confidence score for its classification decision. The classifier having the highest confidence score is the likely class for the data. The SVM may include a system of binary classifiers, where one classifier determines if the driver is in a cognitive tunneling state, or another state, a second classifier determines if the driver is in a fatigue state, or another state, and a third classifier determines if the driver is in another state. The classifier having the highest confidence score represents the likely driver state.

Sensor data for a driver state 1811 may include: medication status based on medication half-life, head motion—head droop, head falling down, Yaw, Pitch; facial features including yawning; body posture in seat; heart rate variability (high, low, resting); facial blood flow (high, normal); eye gaze direction (straight ahead, left, right, down), eye movement (steady, moving), and PERCLOS (percentage).

In S1631, a determination is made as to whether physical and mental state of the driver as determined using sensors is within a tolerance range. If one or more physical and mental state is within a tolerance of side effects determined by the machine learning model (S1631, Pass), a questionnaire of common side effects is provided to the driver. If the state is not within a tolerance of side effects determined by the machine learning model (S1631, Fail), in S1633, the driver may request a questionnaire in order to verify the results of the decision step S1631. The questionnaire, S1635, asks the driver a series of questions.

In some embodiments, the mobile application 513 or vehicle navigation device 702 will provide an inquiry in the form of a displayed message or an audible statement. The inquiry may be a question such as "Are you Sleepy?" The mobile application 513 or vehicle navigation device 702 may provide an inquiry such as "is your vision blurry?" The mobile application 513 or vehicle navigation device 702 may provide an inquiry such as "are you feeling dizzy or light-headed?" The mobile application 513 or vehicle navigation device 702 may provide an inquiry such as "are you finding your movement difficult?" The mobile application 513 or vehicle navigation device 702 may provide an inquiry such as "do you find it difficult to focus or concentrate?"

The mobile application 513 or vehicle navigation device 702 may provide an inquiry, such as "do you have a stomach ache?" In some embodiments, the mobile application 513 or vehicle navigation device 702 may provide a further inquiry, such as "can you drive with driver assist?

In S1637, a check is made as to whether an answer in the questionnaire indicates failure. If the questionnaire is failed (S1637, fail), in S1641, negative feedback will be provided to the machine learning model. If the questionnaire is passed (S1637, pass), in S1639, positive feedback will be provided to the machine learning model.

In S809, a decision is made as to whether the driver is fit to drive. A fitness of a driver to drive may be based on the level of automated driving of a vehicle. A vehicle having a high level of automation may provide functions that alleviate or augment the driver's capacity to drive, while lower levels of automation may require greater capacity of a driver. Also, side effects such as drowsiness or dizziness may be so severe such that a driver may not have sufficient capacity to drive irrespective of the level of automation of a vehicle in all but the highest level of automated driving. If it is determined that the driver is currently not fit to drive (NO in S809), in S811, the vehicle will not be started.

In one embodiment, side effects including drowsiness or sleepiness, blurred vision, dizziness, and fainting may be a high degree of driver impairment. This high degree of driver impairment may require that the vehicle not be driven by the driver until the side effects are sufficiently alleviated. In such case, the driver may have to consider alternative forms of transportation, such as rides with another person as the driver, taking a taxi cab, riding in a shuttle bus or van, or a form of public transportation.

In one embodiment, after a period of time the driver may decide that they are feeling better and may wish to proceed to re-perform the check. FIG. 16B is a flowchart for re-performing the startup check, S807. In S1651, the driver may enter into the mobile application 513 or vehicle navigation device 702, an indication that they are feeling better and would like to proceed with the startup check. In S1653, the mobile application 513 or vehicle navigation device 702 may perform the startup check of FIG. 16A.

Otherwise, the vehicle may be started (YES in S809), but, in S813, the driver will be continuously monitored. Driver monitoring is a dynamic process that continuously cycles through determining medication side effects, acquiring driver facial information, performing eye tracking, monitoring heart rate, and acquiring vehicle information, as necessary. In monitoring the driver, the mobile app 513 or the driver monitor system 300 will check (in S815) whether the driver shows signs of side effects. Side effects from medications may include various degrees or outcomes. Side effects such as slowed movement, inability to focus or concentrate, nausea may vary by amount of slowed movement, amount of inability to focus or concentrate, degree of nausea. Such variations of outcomes of the side effect decision will be provided for training a machine learning model, in S819. In order to determine a degree or outcome of a side effect, a query may be provided to the driver, for example, by asking a question: "are you feeling OK?"

If the response to the question verifies that the side effect is significant enough to warrant limiting the driver's capacity to drive (NO in S817), the mobile app 513 or the driver monitor system 300 may determine, in S821, the level of automated driving of the vehicle. If the level of automated driving is too low (NO in S821), the vehicle may perform a safe pull over operation S825. If the level of automated driving of the vehicle is high (YES in S821), the vehicle may be switched to autonomous driving mode, S823.

In some embodiments, the autonomous driving mode, S823, may be a level of automated driving that depends on the side effects. Side effects including slowed movement, reduced or inability to focus or concentrate, sever nausea, and some other side effects may be associated with a low degree of driver impairment. This low degree of driver impairment may require some amount of driver assist or autonomous piloting in order to safely drive the vehicle. The particular driver assist or autonomous piloting functions may depend on the type or extent of a side effect. Of course a driver may suffer from multiple side effects.

Figure 19:
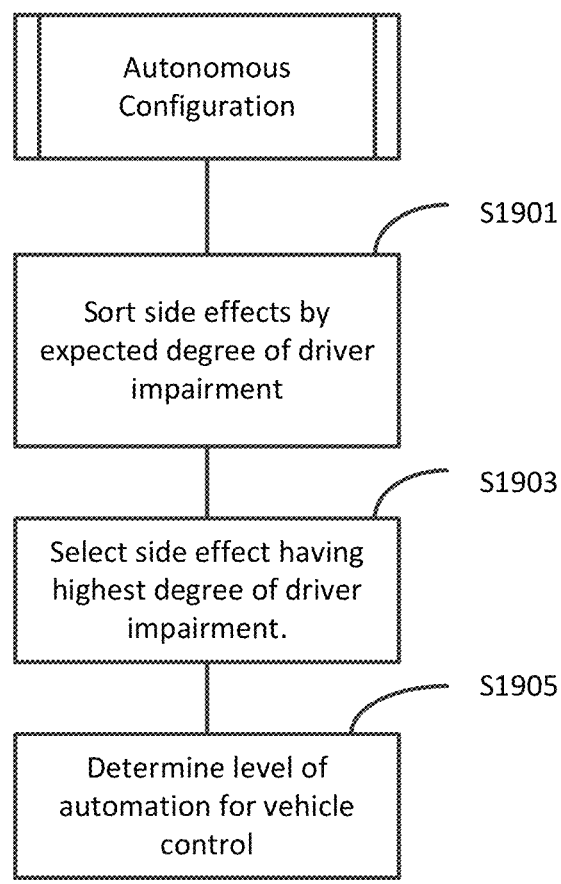
FIG. 19 is a flowchart of selecting a side effect for use in determining a level of automation in accordance with an exemplary aspect of the disclosure.

In some embodiments, when there are multiple side effects, the mobile application 513 or vehicle navigation device 702 may select a side effect. FIG. 19 is a flowchart of selecting a side effect for use in determining a level of automation in accordance with an exemplary aspect of the disclosure.

Some side effects may be more severe than other side effects in their possible effect on a driver's ability to drive. The method in FIG. 19 may result in different levels of automatic driving depending on the expected side effects of medications. A medication may have more than one side effect. Also, the driver may have taken more than one medication, each having one or more side effects. In either case, the level of automatic driving will be based on the side effect that will cause the greatest degree of impairment on the ability of the driver to drive.

Regarding FIG. 19, in S1901, side effects may be sorted by expected degree of driver impairment. Some side effects may have the same expected degree of driver impairment, in which case all side effects having the same degree of driver impairment may be selected in S1903. In S1905, a level of automatic driving will be determined for vehicle control in accordance with the selected side effects.

The particular driver assist or autonomous piloting functions may be selected to augment any deficiency that a driver may have as a result of the side effect. For example, in the case of slowed movement or slow reaction time, external vehicle sensors may monitor nearby vehicles or other objects so that vehicle actions such as breaking or steering may be adjusted as necessary to avoid collision even if the driver is slow to respond. In some embodiments, vehicle functions such as breaking or steering may be completely performed by the vehicle, whereas the driver is required to be attentive in case of emergency or where some automated vehicle functions stop working.

Figure 20:
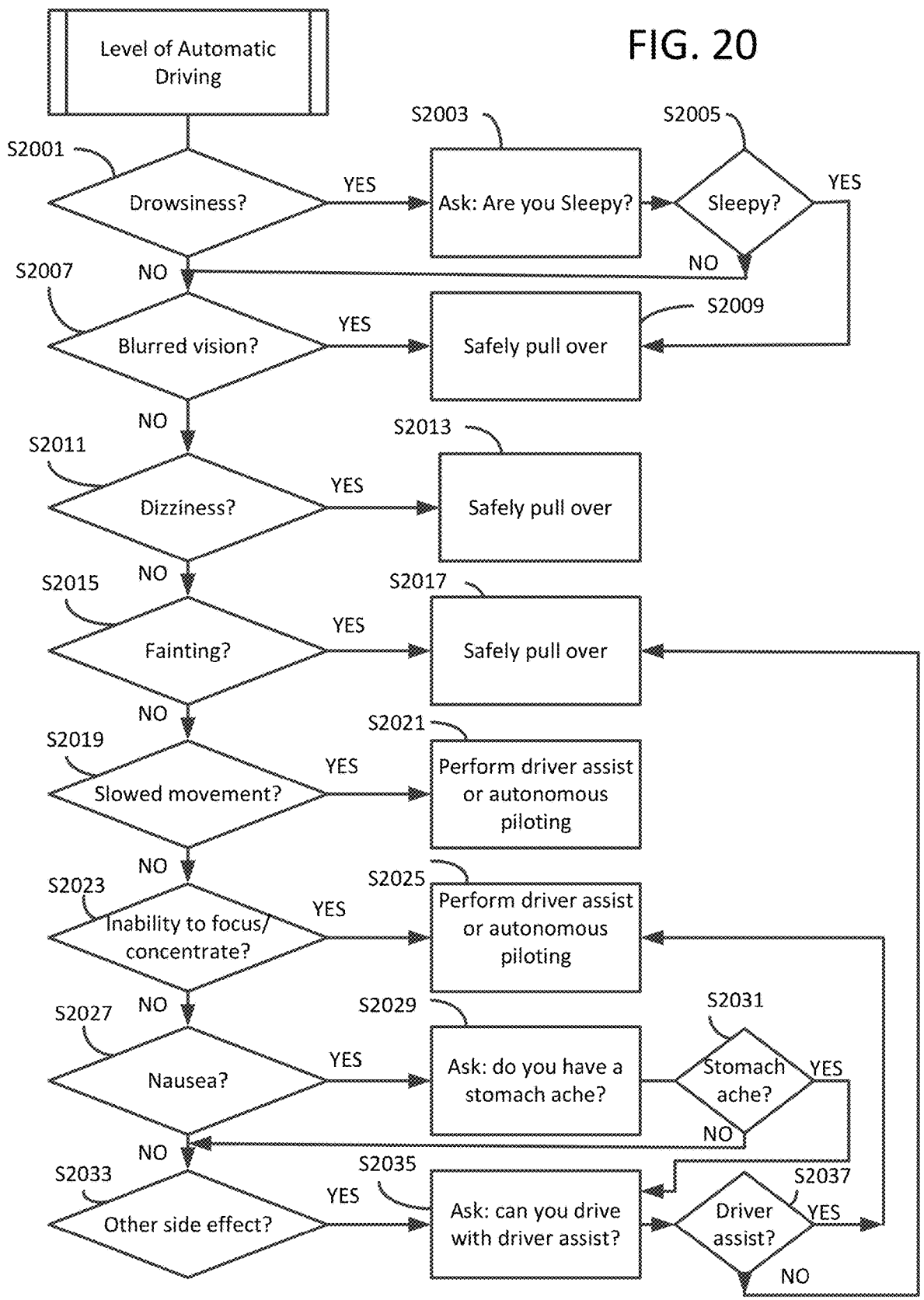
FIG. 20 is a flowchart of a method of determining a level of automatic driving of FIG. 8.

FIG. 20 is a flowchart of a method of determining a level of automatic driving of FIG. 8. The method as shown in FIG.

20 includes a series of decision steps for each type of side effect. It should be understood that other decision steps may be included for additional side effects. Decision steps having the same action step may be combined into a single decision step. In some embodiments, two or more decision steps may be performed in parallel. In some embodiments, decision steps may be proceeded by an inquiry to the driver.

The actions 1825 that may be selected by the agent 1810 may include a stimulus to mitigate a driver state or may include activation of advanced driving safety features, or more strict vehicle actions such as preventing the vehicle from starting or shutting down the vehicle before it is driven, depending on the expected ability of the driver to drive the vehicle or take over driving in the case that an autonomous vehicle requires some degree of manual control.

Regarding FIG. 20, in S2001, a check is made as to whether a side effect is drowsiness/sleepiness. In some embodiments, the mobile application 513 or vehicle navigation device 702 will provide an inquiry in the form of a displayed message or an audible statement. In S2003, the inquiry may be a question such as "Are you Sleepy?" In S2005, the mobile application 513 or vehicle navigation device 702 will detect whether a response from the driver is positive (YES in S2005), or that the driver believes that he/she is not sleepy (NO in S2005). In the case that the driver is drowsy/sleepy, in S2009, the mobile application 513 or vehicle navigation device 702 will send an instruction/command to the vehicle ECU 105 to perform a safe pull over of the vehicle.

In S2007, a check is made as to whether a side effect is blurred vision. Again, the mobile application 513 or vehicle navigation device 702 may provide an inquiry before taking action, then, in S2009, sending an instruction/command to the vehicle ECU 105 to safe pull over of the vehicle.

In S2011, a check is made as to whether a side effect is dizziness. Again, the mobile application 513 or vehicle navigation device 702 may provide an inquiry before taking action, then, in S2013, sending an instruction/command to the vehicle ECU 105 to perform safe pull over of the vehicle.

In S2015, a check is made as to whether a side effect is fainting. Again, the mobile application 513 or vehicle navigation device 702 may provide an inquiry before taking action such as, in S2017, sending an instruction/command to the vehicle ECU 105 to shut down the vehicle or prevent the vehicle from being started.

In S2019, a check is made as to whether a side effect is slowed movement. Again, the mobile application 513 or vehicle navigation device 702 may provide an inquiry before taking action, then, in S2021, sending an instruction/command to the vehicle ECU 105 to perform driver assist functions or autonomous piloting of the vehicle 100. Driver assist functions may include stepped up breaking when the vehicle 100 is within a certain distance from another vehicle being followed. Driver assist functions may include anticipating movement of the steering wheel based on a foreseen curve in the road.

In S2023, a check is made as to whether a side effect is a reduced ability to focus or concentrate. Again, the mobile application 513 or vehicle navigation device 702 may provide an inquiry before taking action such as, in S2025, sending an instruction/command to the vehicle ECU 105 to perform driver assist functions or autonomous piloting of the vehicle 100.

In S2027, a check is made as to whether a side effect is nausea. The mobile application 513 or vehicle navigation device 702 may provide an inquiry, such as S2029 of "do you have a stomach ache?" In some embodiments, the mobile application 513 or vehicle navigation device 702 may provide a further inquiry, such as S2035 of "can you drive with driver assist? If so (YES in S2031 and S2037), in S2025, the mobile application 513 or vehicle navigation device 702 may send an instruction/command to the vehicle ECU 105 to perform driver assist functions or autonomous piloting of the vehicle 100.

In S2033, a check is made as to whether there is another side effect. Again, the mobile application 513 or vehicle navigation device 702 may provide an inquiry, such as S2035 of "can you drive with driver assist?" If so (YES in S2037), in S2025, the mobile application 513 or vehicle navigation device 702 may send an instruction/command to the vehicle ECU 105 to perform driver assist functions or autonomous piloting of the vehicle 100.

Numerous modifications and variations of the present invention are possible in light of the above teachings. It is therefore to be understood that within the scope of the appended claims, the invention may be practiced otherwise than as specifically described herein.

The invention claimed is:

1. A driver monitor system for predicting impairment of a user of a vehicle, the system comprising:
   at least one video camera;
   an input output device for inputting a list of at least one medication being taken by the user of the vehicle; and
   processing circuitry configured to:
   predict at least one side effect of the at least one medication based on the half-life of the at least one medication,
   detect eye gaze movement, eye lid position, and facial expression of the user using images from the at least one video camera,
   use the eye gaze movement, eye lid position, and facial expression to predict whether the user is transitioning into an impaired physical state that is a side effect of the at least one medication,
   verify the at least one side effect of the at least one medication,
   determine whether the user is fit to drive using the verified at least one side effect of the at least one medication, and
   output to the vehicle an instruction to operate the vehicle in a level of automation that makes up for the at least one side effect or to perform a safe pull over operation of the vehicle.

2. The driver monitor system of claim 1, wherein the input output device is configured to display a status list of the at least one medication and a most recent time that the at least one medication had been taken by the user.

3. The driver monitor system of claim 2, wherein the input output device is configured to add a medication to the status list of the at least one medication.

4. The driver monitor system of claim 2, wherein the processing circuitry is configured to predict at least one side effect of the at least one medication based on the half-life of the medication by determining if the half-life of the at least one medication has been reached using the most recent time that the at least one medication had been taken by the driver.

5. The driver monitor system of claim 1, further including a machine learning device,
   wherein the input output device outputs a verification request and receives a response to the verification request, and
   wherein the eye gaze movement, the eye lid position, and the facial expression are fed back to the machine learning device which learns to predict whether the driver is transitioning into an impaired physical state.

6. The driver monitor system of claim 5, wherein parameters of the machine learning device that are learned are stored in a memory as a profile associated with the user.

7. The driver monitor system of claim 6, wherein independent profiles are stored in the memory in association with respective different users.

8. The driver monitor system of claim 5, wherein the processing circuitry further monitors eye gaze movement, and
wherein the eye gaze movement is fed back to the machine learning device which learns to predict whether the driver is transitioning into an impaired physical state.

9. The driver monitor system of claim 5, wherein the machine learning device learns by performing a reinforcement learning algorithm.

10. The driver monitor system of claim 1, wherein the processing circuitry is configured to predict a side effect of the at least one medication including sorting side effects by expected degree of user impairment, and to select at least one side effect having a highest degree of user impairment.

11. A method of predicting impairment of a driver of a vehicle by a driver monitor system including at least one video camera, an input output device for inputting a list of at least one medication being taken by the driver of the vehicle, and processing circuitry, the method comprising:
predicting at least one side effect of the at least one medication based on the half-life of the at least one medication,
detecting, by the processing circuitry, eye gaze movement, eye lid position, and facial expression using images from the at least one video camera;
using the eye gaze movement, eye lid position, and facial expression to predict, by the processing circuitry, whether the user is transitioning into an impaired physical state;
verifying the at least one side effect of the at least one medication;
determining whether the user is fit to drive using the verified at least one side effect of the at least one medication; and
outputting to the vehicle an instruction to operate the vehicle in a level of automation that makes up for the at least one side effect or to perform a safe pull over operation of the vehicle.

12. The method of claim 11, further comprising:
displaying, by the input output device, a status list of the at least one medication and a most recent time that the at least one medication had been taken by the user.

13. The method of claim 12, further comprising:
adding, by the input output device, a medication to the status list of the at least one medication.

14. The method of claim 12, further comprising:
predicting, by the processing circuitry, at least one side effect of the at least one medication based on the half-life of the medication by determining if the half-life of the at least one medication has been reached using the most recent time that the at least one medication had been taken by the user.

15. The method of claim 11, the system further including a machine learning device, the method further comprising:
outputting, by the input output device, a verification request and receiving a response to the verification request; and
feeding back the eye gaze movement, the eye lid position, and the facial expression to the machine learning device which learns to predict whether the driver is transitioning into an impaired physical state.

16. The method of claim 15, further comprising:
storing in a memory parameters of the machine learning device that are learned as a profile associated with the user.

17. The method of claim 16, further comprising:
storing in the memory independent profiles in association with respective different users.

18. The method of claim 15, further comprising:
monitoring, by the processing circuitry, eye gaze movement, and
feeding back the eye gaze movement to the machine learning device which learns to predict whether the driver is transitioning into an impaired physical state.

19. The method of claim 15, wherein the machine learning device learns by performing a reinforcement learning algorithm.

20. The method of claim 11, wherein the predicting a side effect of the at least one medication includes sorting side effects by expected degree of user impairment, and selecting at least one side effect having a highest degree of user impairment.

* * * * *